United States Patent

Matsui et al.

Patent Number: 5,468,421
Date of Patent: Nov. 21, 1995

[54] CYCLOHEXANE DERIVATIVE AND LIQUID CRYSTAL COMPOSITION CONTAINING THE SAME

[75] Inventors: Shuichi Matsui; Yasuyuki Goto; Yuichi Onji; Atsuko Fujita, all of Chiba, Japan

[73] Assignee: Chisso Corporation, Ohsaka, Japan

[21] Appl. No.: 53,417

[22] Filed: Apr. 28, 1993

[30] Foreign Application Priority Data

Apr. 28, 1992 [JP] Japan ................... 4-110351

[51] Int. Cl.⁶ ............. C02K 19/30; C07C 255/50; C07C 25/13
[52] U.S. Cl. .............. 252/299.63; 558/411; 558/425; 570/127; 568/647
[58] Field of Search ............ 570/127; 568/631, 568/647; 558/411, 425; 585/25; 252/299.63

[56] References Cited

U.S. PATENT DOCUMENTS

| | | | |
|---|---|---|---|
| 4,877,548 | 10/1989 | Kitano et al. | 252/299.63 |
| 5,032,313 | 7/1991 | Goto et al. | 252/299.63 |
| 5,288,428 | 2/1994 | Kelly | 252/299.63 |
| 5,346,647 | 9/1994 | Kelly et al. | 252/299.63 |
| 5,370,822 | 12/1994 | Matsui et al. | 252/299.63 |
| 5,401,434 | 3/1995 | Fujita et al. | 252/299.63 |

FOREIGN PATENT DOCUMENTS

| | | |
|---|---|---|
| 0280902 | 9/1988 | European Pat. Off. . |
| 0410233 | 1/1991 | European Pat. Off. . |
| 0480217 | 4/1992 | European Pat. Off. . |
| WO92/13928 | 8/1992 | WIPO . |

Primary Examiner—Shean Wu
Attorney, Agent, or Firm—Wenderoth, Lind & Ponack

[57] ABSTRACT

A liquid crystalline compound which has a low viscosity and is electrically and chemically stable and compatible with other known liquid crystalline compounds at low temperatures, and a liquid crystal composition containing the same, which compound is a phenyl-4-cyclohexylbutylcyclohexane derivative expressed by the formula:

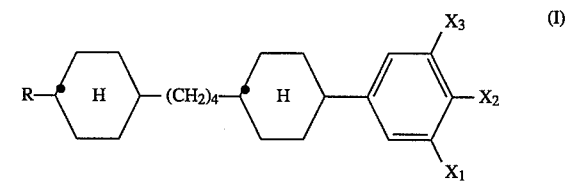

wherein R represents a hydrogen atom or a linear or branched alkyl group of 1 to 15 carbon atoms, and $X_1$, $X_2$ and $X_3$ are each independent and $X_1$ and $X_3$ each represent a hydrogen atom or a halogen atom and $X_2$ represents a hydrogen atom or a linear or branched alkyl group of 1 to 15 carbon atoms (wherein one —$CH_2CH_2$— bond may be replaced by a —CH=CH— bond and one non-adjacent —$CH_2$— bond may be replaced by an oxygen atom), a halogen atom, a cyano group, a trifluoromethyl group or a trifluoromethoxy group.

12 Claims, No Drawings

CYCLOHEXANE DERIVATIVE AND LIQUID CRYSTAL COMPOSITION CONTAINING THE SAME

BACKGROUND OF THE INVENTION

1. Field of the Invention

This invention relates to a cyclohexane derivative, and more particularly it relates to a phenyl-4-cyclohexylbutyl-cyclohexane derivative and a liquid crystal composition containing the same as an effective component.

2. Description of the Related Art

Liquid crystal display elements utilize the optical anisotropy and dielectric aniostropy of liquid crystal substances, and as their display modes, TN mode (twisted nematic mode), super-twisted, nematic mode (STN mode), dynamic scattering mode (DS mode), guest-host mode (G.H. mode), DAP mode, etc. have been known. Further, as the driving mode thereof, static driving mode, multiplex driving mode, active matrix driving mode, two-frequency addressing scheme, etc. have been employed. The properties of the liquid crystal substances required for these various liquid crystal display elements are varied, but any of these liquid crystal substances are commonly required to be stable to moisture, air, heat, light, etc. and also required to exhibit liquid crystal phases within a mesomorphic range as broad as possible around room temperature, have a low viscosity, and exhibit a quick response, a high contrast and further a low driving voltage in the display elements, and also required to have a superior compatibility with other liquid crystalline compounds since the substances are usually used as compositions. Further, it is required to have the optimum dielectric anisotropy value ($\Delta\epsilon$) depending upon the kinds of display elements. However, no liquid crystal compound satisfying these specific features as a single component has been known at present. Hence, it is the present status that liquid crystal compositions obtained by blending several liquid crystalline compounds or non-crystalline compound have been used.

As described above, since a mixture of liquid crystalline compounds are used for compositions, the compatibility thereof is important, and in particular, the compatibility at low temperatures is one of the most important factors for liquid crystal display elements wherein driving within a broad temperature range is required.

As conventional liquid crystal compounds, the following compounds have been disclosed:

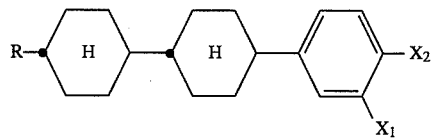

U.S. Pat. No. 4,405,488

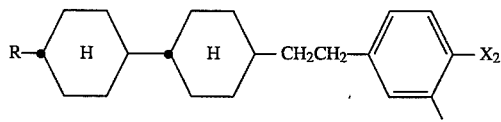

U.S. Pat. No. 4,797,228

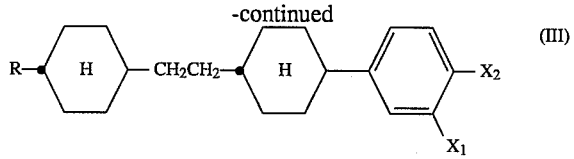

U.S. Pat. No. 4,820,443

Compound of (I) U.S. Pat. No. 4,405,488 has a structure wherein two cyclohexane rings and a benzene ring are directly bonded, and compounds of (II) and (III) have an ethane bond in the molecule, respectively. It has been generally known that the ethane bond linking the core parts (mainly cyclohexane ring and benzene ring) of usual liquid crystal molecules has an effect of retaining the compatibility at low temperatures without raising the viscosity, but even in the case of compounds having the same ethane bond, when the case of linking cyclohexane ring and benzene ring (compound (II)) is compared in the aspect of properties, with the case of linking cyclohexane ring and cyclohexane ring (compound (III)), the result is different. Namely, in the case of compound (III), a sufficient effect of low temperature compatibility can be obtained by inserting the ethane bond, as compared with the case of compound (I), whereas in the case of compound (II), the effect is insufficient. Further, Japanese patent application laid-open No. Hei 3-66632 discloses the following compound wherein cyclohexane ring and benzene ring are linked by a linear butane bond:

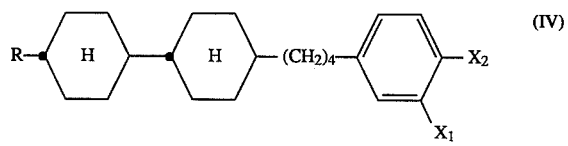

In the case of compound (IV), according to the report of its properties, its smectic properties are strong, and the effect of compatibility by butane bond inserted as a linking group for cores of a liquid crystalline molecule, with other liquid crystalline compounds, particularly at low temperatures, is insufficient.

Thus, the present inventors have investigated introduction of an alkyl group into the core-linking part of the liquid crystalline molecule, and as a result, have found that when two cyclohexane groups are linked with butane bond, the smectic phase is suppressed, the nematic phase is broadened and also the compatibility at low temperatures is improved. Thus, the compounds recited in the instant claims as novel liquid crystalline substances have been invented.

SUMMARY OF THE INVENTION

The object of the present invention is to provide a novel liquid crystalline compound which has a low viscosity, is electrically and chemically stable and has a superior compatibility with other known liquid crystalline compounds at low temperatures, and a liquid crystal composition containing the same.

The present invention resides in:

a phenyl-4-cyclohexylbutylcyclohexane derivative expressed by the formula

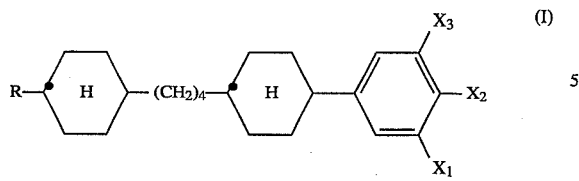

wherein R represents a hydrogen atom or a linear or branched alkyl group of 1 to 15 carbon atoms, and $X_1$, $X_2$ and $X_3$ are each independent and $X_1$ and $X_3$ each represent a hydrogen atom or a halogen atom and $X_2$ represents a hydrogen atom or a linear or branched alkyl group of 1 to 15 carbon atoms (wherein one —$CH_2CH_2$— bond may be replaced by a —CH=CH— bond and one non-adjacent —$CH_2$— bond may be replaced by an oxygen atom), a halogen atom, a cyano group, a trifluoromethyl group or a trifluoromethoxy group, and a liquid crystal composition containing the above compound as an effective component.

The liquid crystal composition provided by the present invention is preferred to be a liquid crystal dielectric comprising a component (A) containing at least one compound expressed by the formula (I), and besides, a component (B) containing at least one compound having a high dielectric anisotropy value of $\Delta\epsilon \geq 5$, a component (C) having a low dielectric anisotropy value of $|\Delta\epsilon| < 5$, and a component (D) containing at least one compound having a clearing point exceeding 80° C., and if necessary, another component (E).

DETAILED DESCRIPTION OF PREFERRED EMBODIMENTS

Preferable compounds for the component (B) of the liquid crystal composition of the invention are shown below.

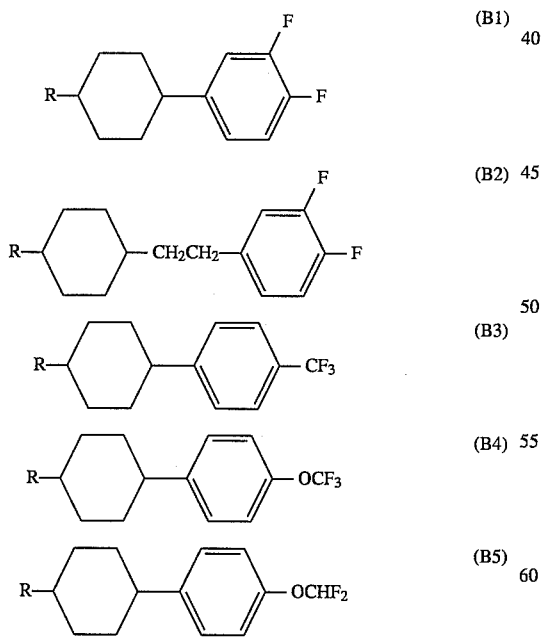

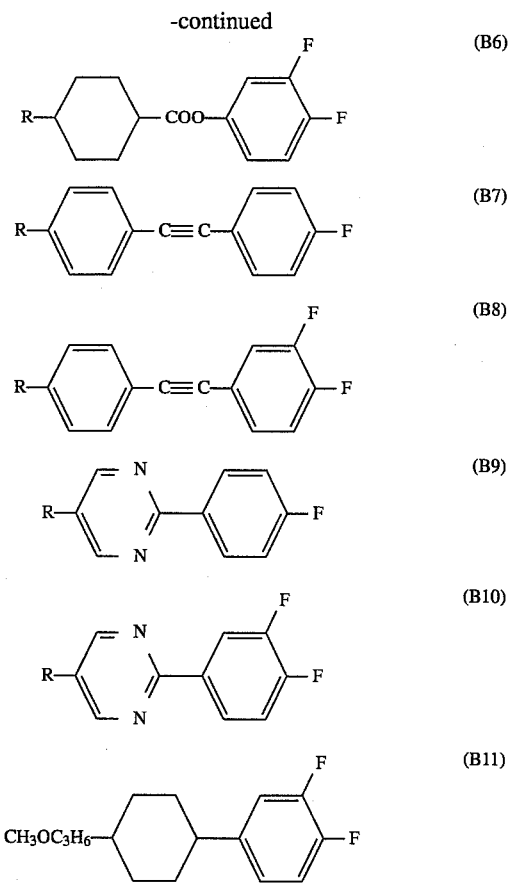

In the above compounds, R represents an alkyl group or an alkenyl group of 1 to 10 carbon atoms, and one carbon atom of the groups or two carbon atoms not adjacent to each other in the group may be replaced by oxygen atom(s).

Preferable compounds for the component (C) are shown below.

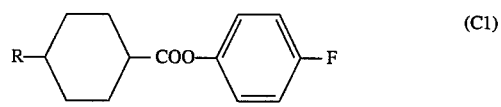

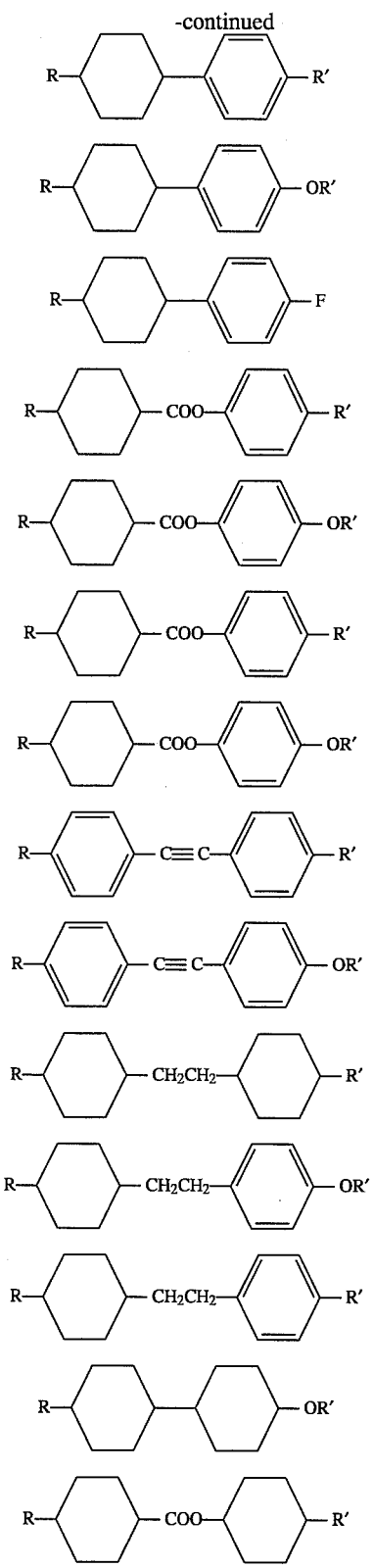
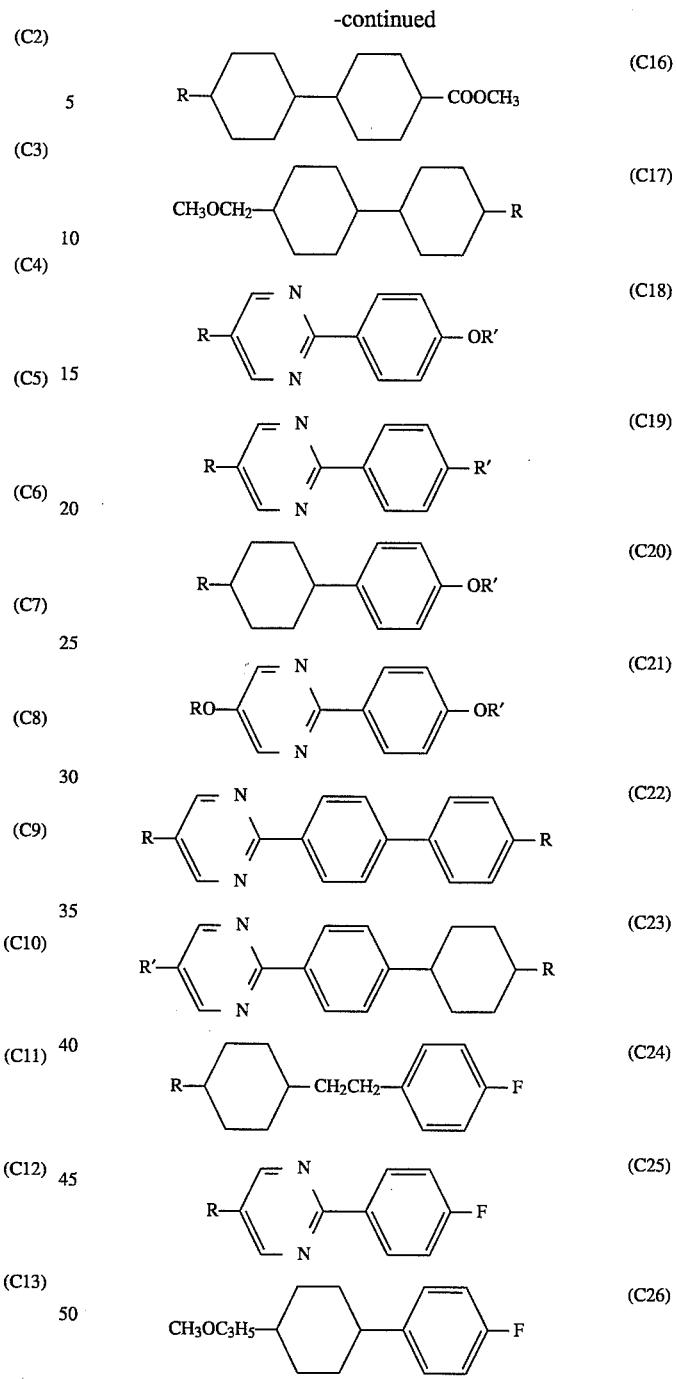
In these compounds, R and R' represent an alkyl group or alkenyl group of 1 to 10 carbon atoms, and one carbon atom of the groups or two carbon atoms not adjacent to one another in the group may be replaced by oxygen atom(s).
Preferable compounds for the component (D) are shown below.

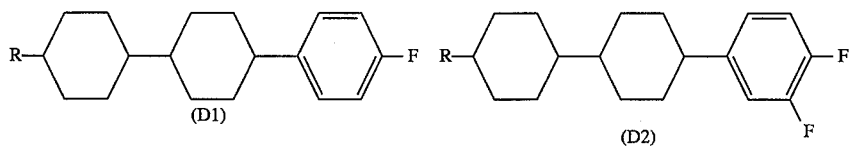
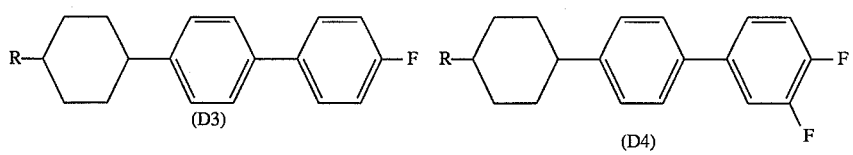
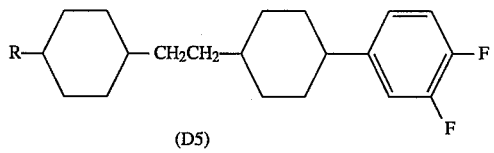
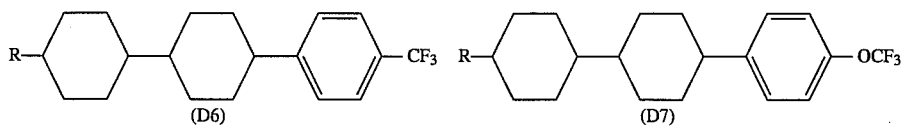
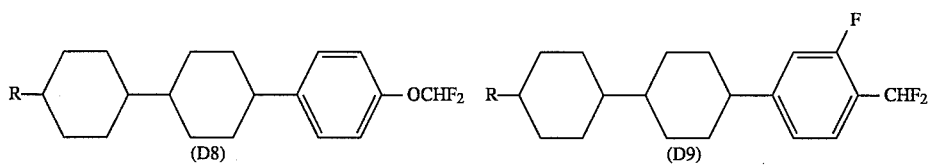
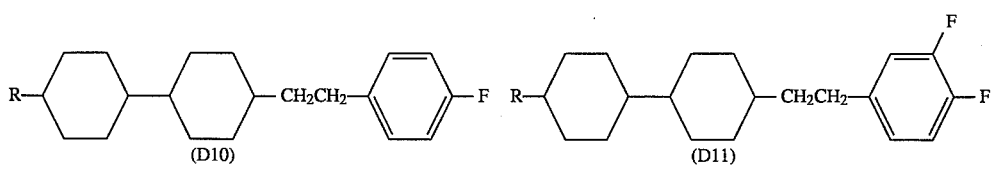
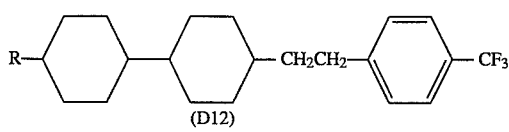
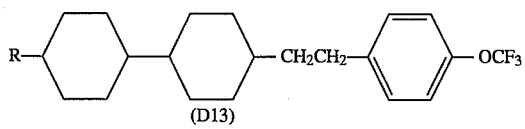
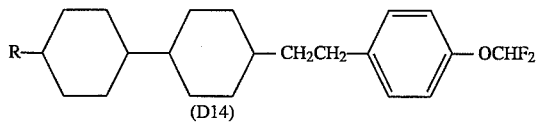
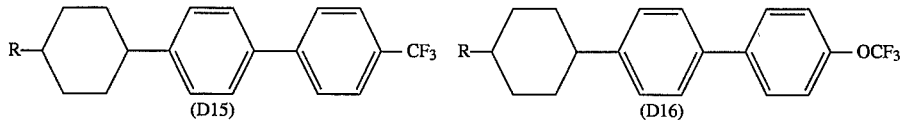
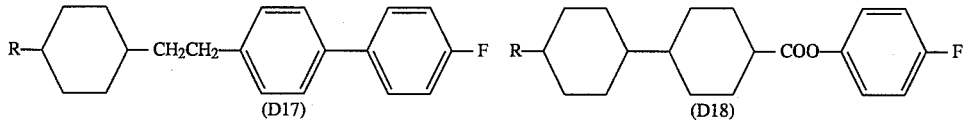

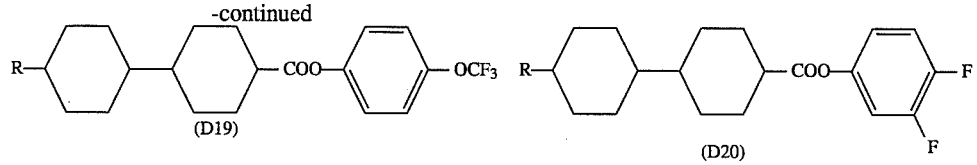
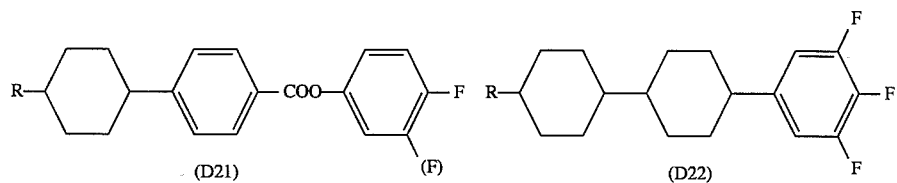
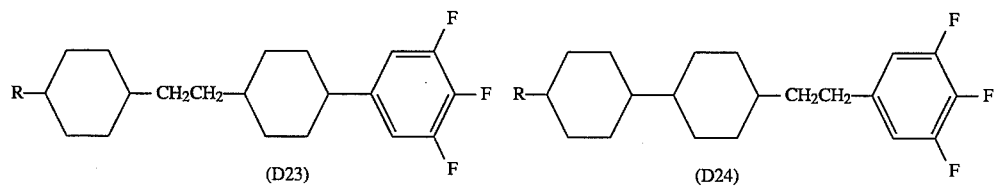
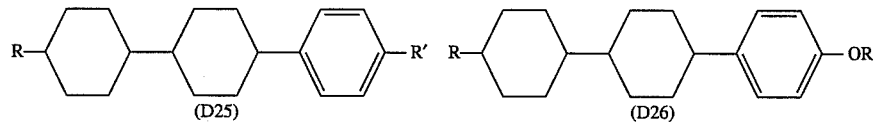
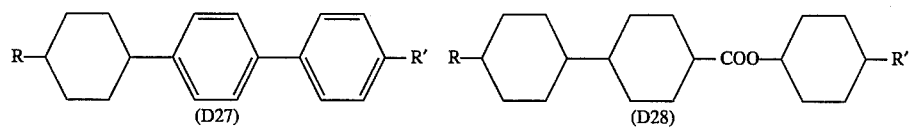
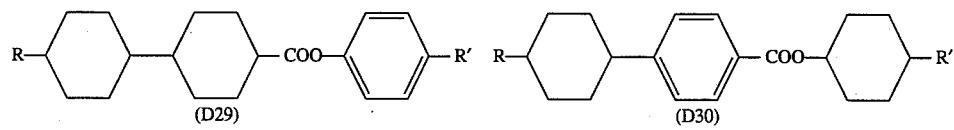
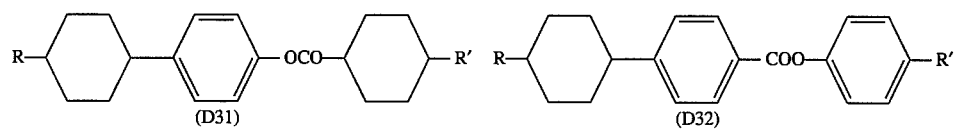
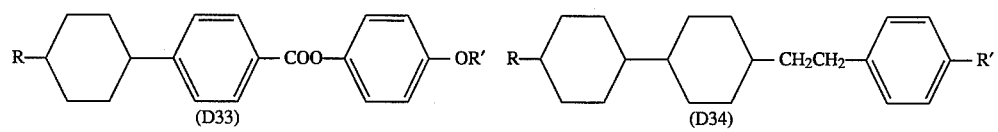
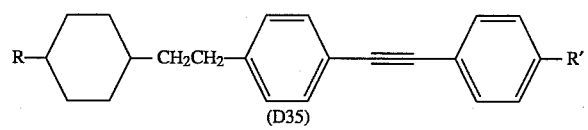
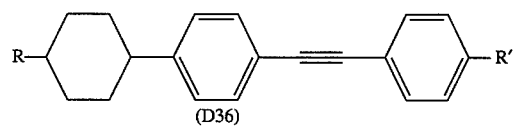
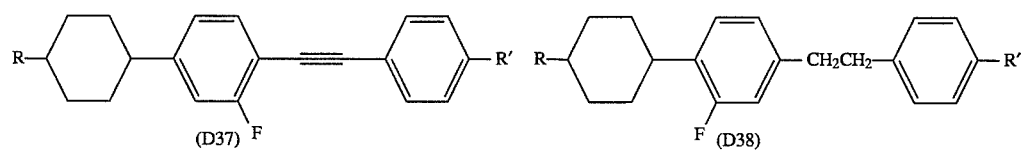

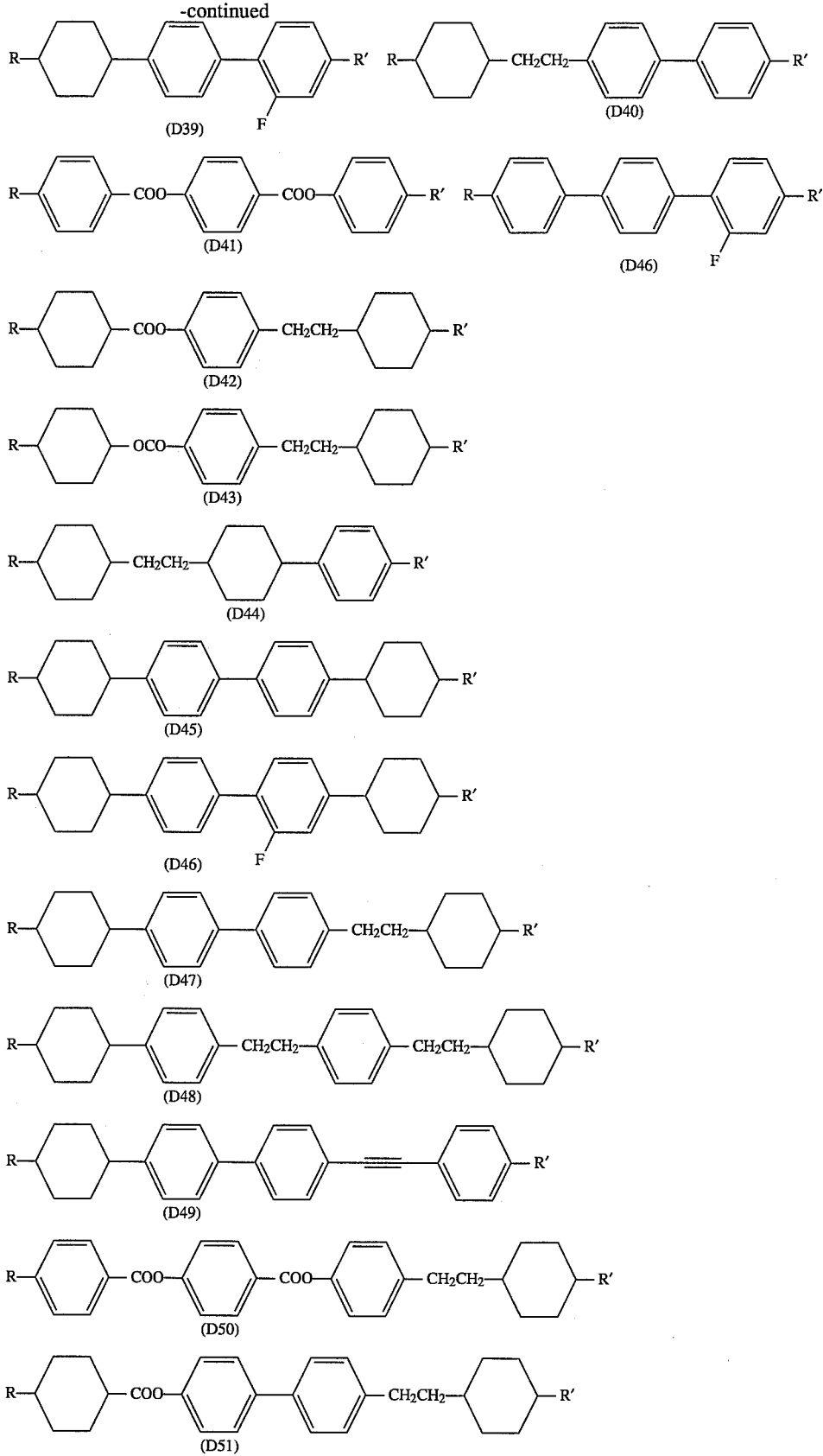

-continued
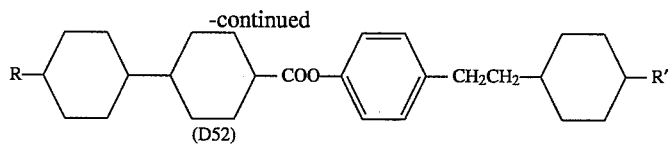
(D52)
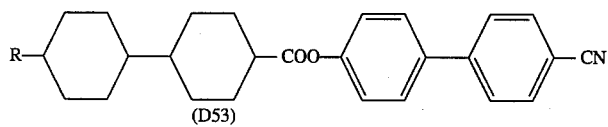
(D53)
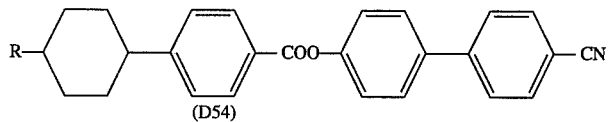
(D54)
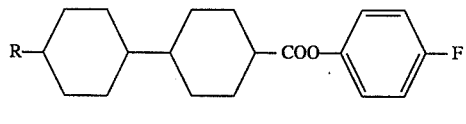
(D55)
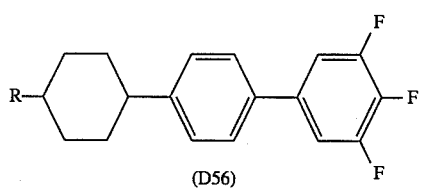
(D56)
In the above compounds, R and R' represent an alkyl group or alkenyl group of 1 to 10 carbon atoms, and one carbon atom of the group or two carbon atoms not adjacent to one another in the group may be replaced by oxygen atom(s).
Preferable compounds for the component (E) are shown below.
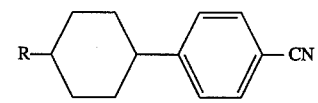
(E1)
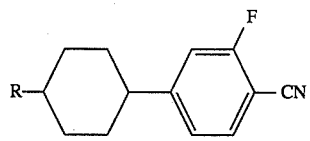
(E2)
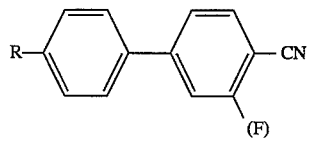
(E3)
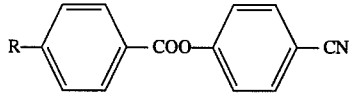
(E4)
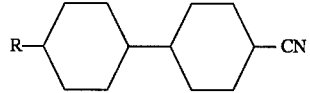
(E5)
-continued
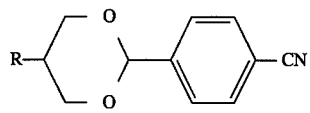
(E6)
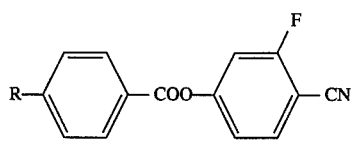
(E7)
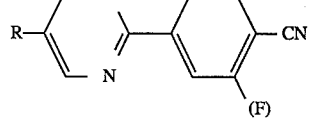
(E8)
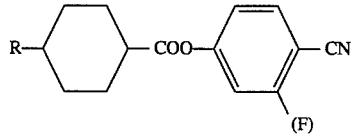
(E9)
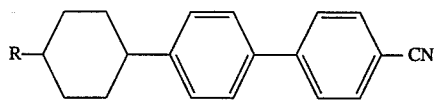
(E10)

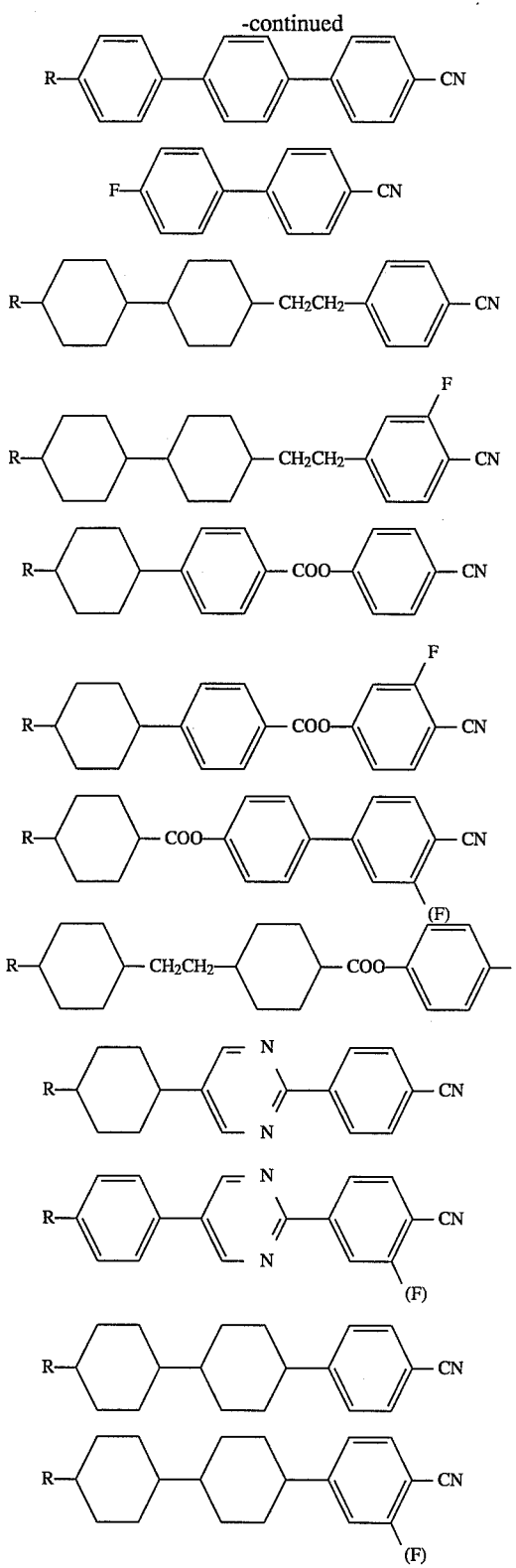

In the above compounds, R represents an alkyl group or alkenyl group of 1 to 10 carbon atoms, and one carbon atom of the groups or two carbon atoms not adjacent to one another in the group may be replaced by oxygen atom(s).

The composition according to the present invention contains at least one compound expressed by the formula (I) preferably in a proportion of 0.1 to 40% by weight in order to obtain superior liquid crystalline characteristics.

Preferred examples of the compound (I) of the present invention are those expressed by the following formula (I-a)–(I-s).

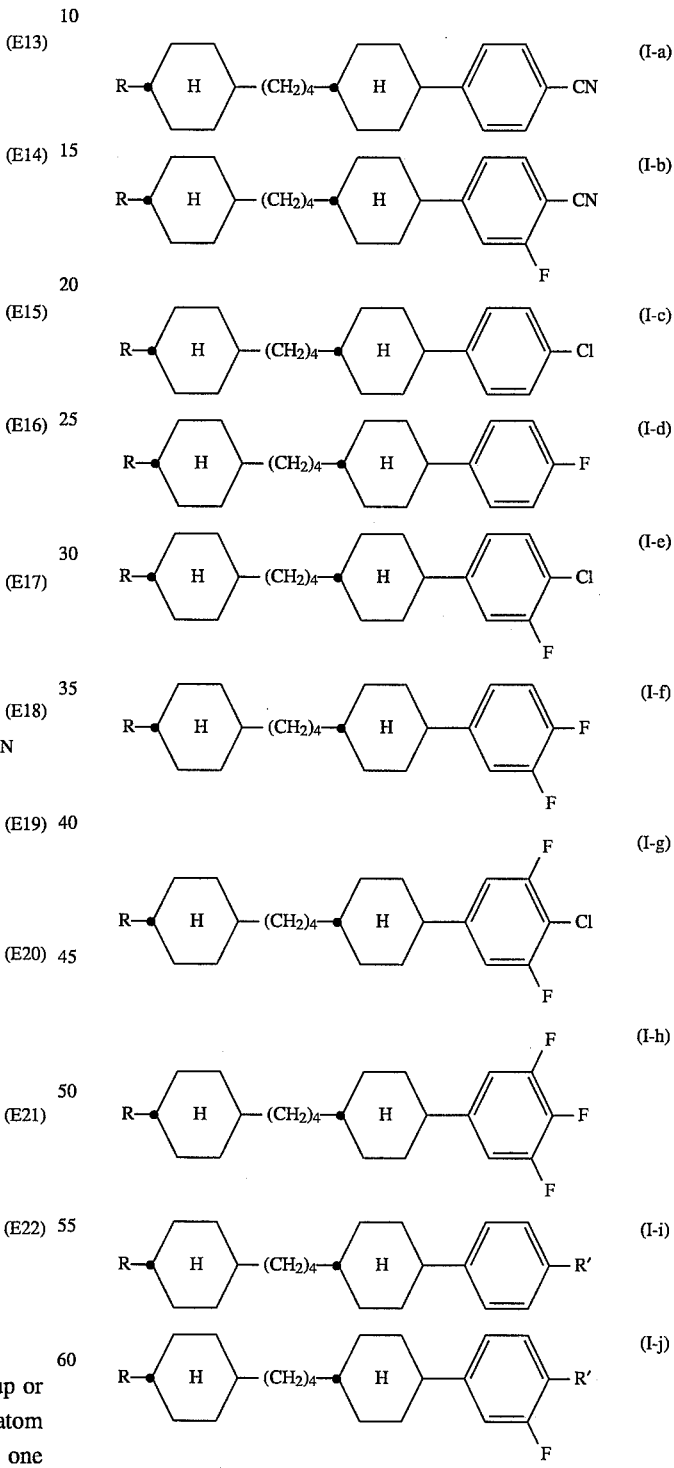

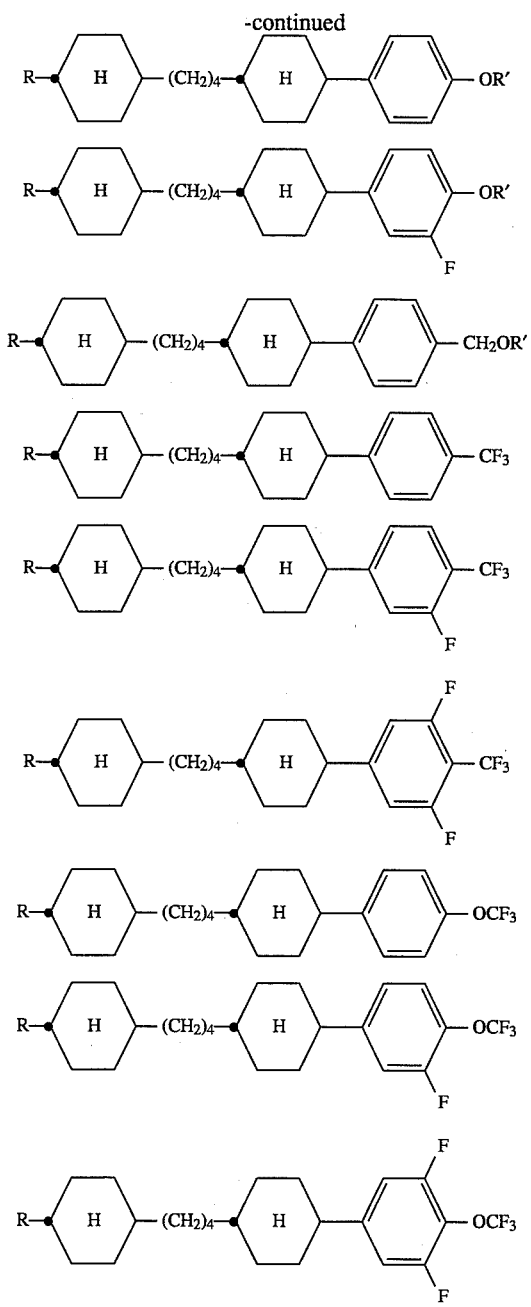

The above R and R' each independently represent a hydrogen atom or a linear or branched alkyl group of 1 to 15 carbon atoms.

Compounds (I-a) and (I-b) each having a cyano group at the terminal end thereof have a large positive dielectric anisotropy value Δε, and compounds (I-d), (I-e), (I-f), (I-g) and (I-h) each having fluorine atom(s) at the terminal end thereof have a large positive dielectric anisotropy value Δε and nevertheless have a low viscosity. Further, compounds (I-n), (I-o), (I-p), (I-q), (I-r) and (I-s) each having a trifluoromethyl group or a trifluoromethoxy group are chemically very stable and useful as a liquid crystalline material for an active matrix display needing a high retention percentage, and being expected to be developed in the future and as a component for constituting the liquid crystal composition therefor.

The compound of the present invention is electrically stable and also stable to heat, air, light, etc. and further, by choosing various substituents thereof, a compound having an adequate dielectric anisotropy value can be obtained. Further, the compound of the present invention has a superior compatibility with other liquid crystalline compounds, in particular a superior compatibility at low temperatures, and can provide a liquid crystal material having improved characteristics.

(Preparation of the compound)

Next, the preparation of the compound of the present invention can be divided into 2 steps, that of a 4-[4-(trans-4-alkylcyclohexyl)butyl] cyclohexanone 14 as a raw material for preparing the compound and that of the respective compounds using the same.

The preparation of the 4-[4-(trans-4-alkylcyclohexyl)butyl]cyclohexanone 14 as a raw material for preparing the compound is as follows:

A trans-4-alkylcyclohexylacetyl chloride 1 is converted into an ester 2, followed by reducing it with lithium aluminum hydride into an alcohol substance 3, brominating this 3 with hydrobromic acid into a brominated substance 4, cyanating it with sodium cyanide in DMSO, to prepare a 1-cyano-2-(4-transalkylcyclohexyl) ethane 5. This nitrile substance 5 is hydrolyzed into a carboxylic acid derivative 6, followed by esterifying it in the presence of an acid catalyst, to prepare a 4-(trans-4-alkylcyclohexyl)propanoic acid ethyl ester 7. Further, the ester 7 is subjected to once more repetition of the deriving operations from 2 to 6, a 4-(trans-4-alkylcyclohexyl)butanoic acid 8 having the number of carbon atoms increased by one is derived, followed by reacting thionyl chloride therewith to derive it into a 4-(trans-4-alkylcyclohexyl)butyl chloride 9. This acid chloride derivative 9 is reacted with a Grignard reagent prepared from 4-bromoanisole in the presence of iron (III) acetylacetonate to obtain a 4-(trans-4-alkylcyclohexyl)-1-(4-methoxyphenyl)butan-1-one 10, followed by reducing it with lithium aluminum hydride in the presence of aluminum chloride to obtain a 1-(4-transalkylcyclohexyl)-4-(4-methoxyphenyl)butane 11, reacting this 11 with boron tribromide in dichloromethane, to prepare a phenol derivative 12. The nucleus of 12 is hydrogenated in the presence of a palladium-barium sulfate catalyst in cyclohexane under pressure to obtain a cyclohexanol derivative 13, followed by oxidizing the derivative 13 with an aqueous solution of sodium hypochlorite in a halogenated hydrocarbon, to prepare the objective 4-[4-(trans-4-alkylcyclohexyl)butyl]cyclohexanone 14.

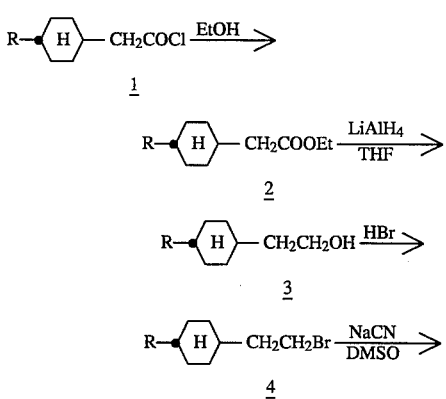

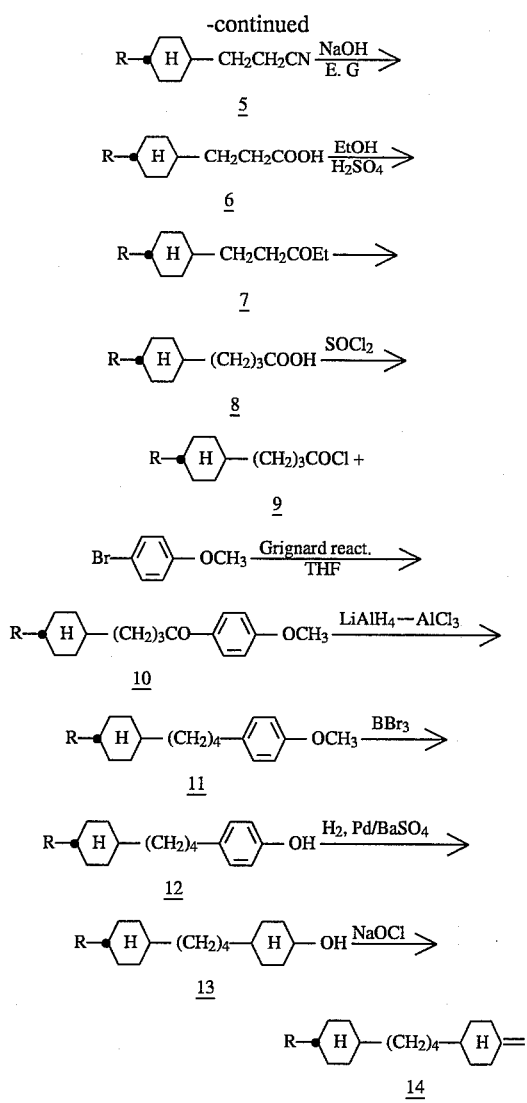

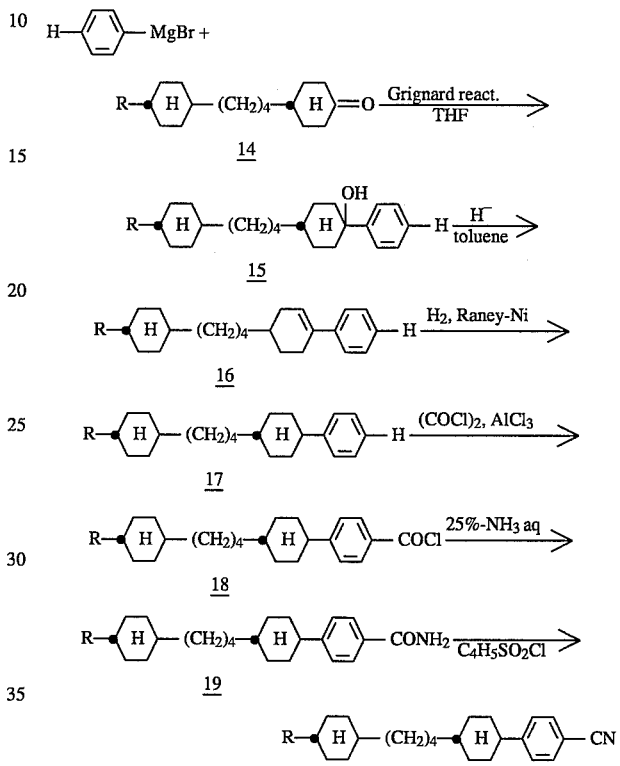

dichloromethane, to prepare a 4-[trans-4-[4-(4-transalkylcyclohexyl)butyl]cyclohexyl]benzoyl chloride 18, reacting this benzoyl chloride 18 with aqueous ammonia to prepare an acid amide substance 19, and reacting this 19 with benzenesulfonyl chloride in pyridine to obtain the objective 4-[trans-4-[4-(4-transalkylcyclohexyl)butyl]-cyclohexyl]benzonitrile.

Using the thus prepared 4-[4-(trans-4-alkylcyclohexyl)butyl]cyclohexanone 14 as a raw material, various phenyl-4-cyclohexylbutylcyclohexane derivatives can be prepared. For example, the compound expressed by the above formula (I-a) can be prepared according to the following process.

Namely, bromobenzene is reacted with flaked magnesium in tetrahydrofuran (hereinafter abbreviated to THF) to prepare a Grignard reagent, followed by reacting this Grignard reagent with a 4-[4-(trans-4-alkylcyclohexyl)butyl]cyclohexanone 14 to prepare an alcohol substance 15, subjecting this 15 to dehydration reaction using an acidic ion exchange resin for non-aqueous use, as a catalyst, to prepare a phenyl-4-[4-(4-transalkylcyclohexyl)butyl]cyclohexene 16, subjecting it to catalytic reduction under pressure, using Raney-Ni catalyst, and further recrystallizing the trans substance thereof to prepare a phenyl-4-[4-(4-transalkylcyclohexyl)butyl]transcyclohexane 17, reacting this 17 with oxalyl chloride using anhydrous aluminum chloride as a catalyst in Further, for example, a compound expressed by (I-b) can be prepared according to the following process.

Namely, 3-fluorobromobenzene is reacted with flaked magnesium in THF to prepare a Grignard reagent, followed by reacting this Grignard reagent with a 4-[4-(trans-4-alkylcyclohexyl)butyl]cyclohexanone 14 to prepare an alcohol substance 20, subjecting this 20 to dehydration reaction using an acidic ion-exchange resin for non-aqueous use as a catalyst to obtain a 4-[4-[4-(4-transalkylcyclohexyl)butyl]cyclohexen-1-yl]-2-fluorobenzene 21, subjecting it to catalytic reduction under pressure using a Raney nickel catalyst and further purifying the resulting trans-form substance by recrystallization to prepare a 4-[4-trans-[4-(4-transalkylcyclohexyl)butyl]cyclohexyl]-2-fluorobenzene 22, reacting oxalyl chloride with this 22 using anhydrous aluminum chloride as a catalyst in dichloromethane to prepare a 4-[4-trans-[4-(4-transalkylcyclohexyl)butyl]cyclohexyl]-2-fluorobenzoyl chloride 23, reacting this 23 with aqueous ammonia to obtain an acid amide substance 24, and reacting this 24 with benzenesulfonyl chloride in pyridine to obtain the objective 4-[4-trans-[4-(4-transalkylcyclohexyl)butyl]cyclohexyl]-2-fluorobenzonitrile.

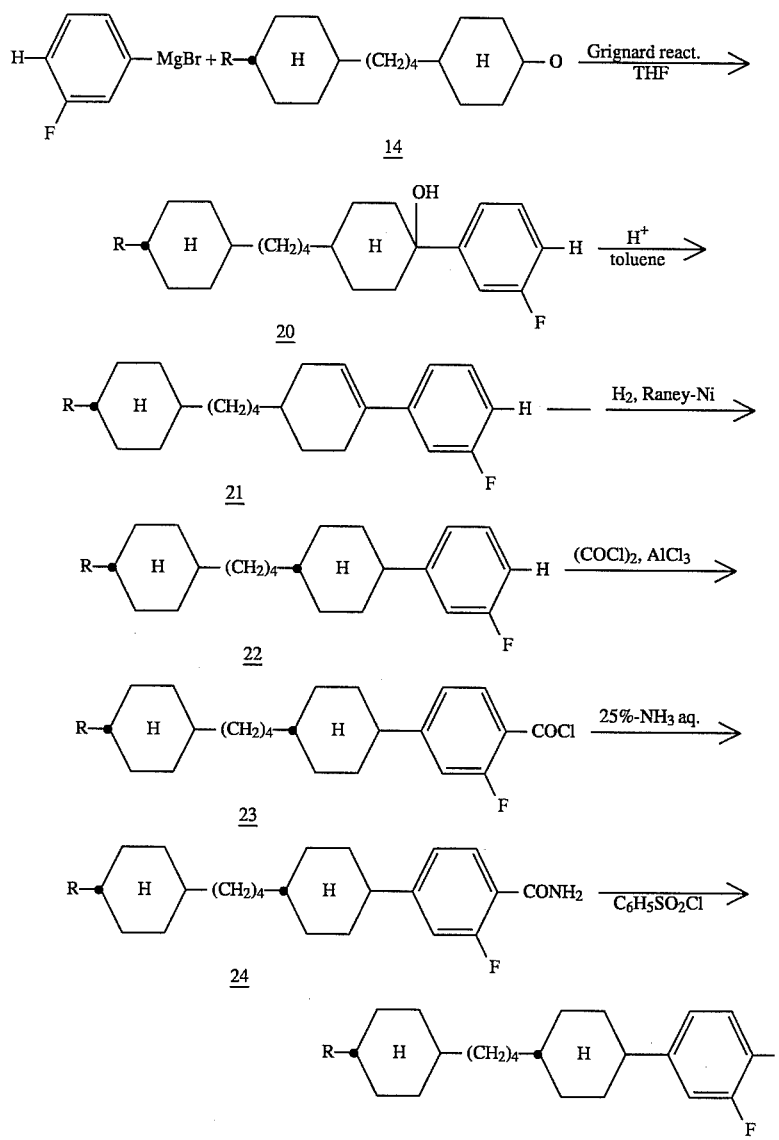

Further, the compound of the present invention (I-d) can be prepared according to the following process, for example.

Namely, 4-bromofluorobenzene is reacted with flaked magnesium in THF to prepare a Grignard reagent, followed by reacting this Grignard reagent with a 4-[4-(trans-4-alkylcyclohexyl)butyl]cyclohexanone 14 to prepare an alcohol substance 25, subjecting it to dehydration reaction using an acidic ion-exchange resin for non-aqueous use as a catalyst to obtain a 4-[4-[4-(4-transalkylcyclohexyl)butyl] cyclohexen-1-yl]fluorobenzene 26, subjecting it to catalytic reduction under pressure using Raney Ni catalyst, and purifying the resulting trans substance by recrystallization to prepare the objective 4-[4-trans-[4-(4-transalkylcyclohexyl)butyl]cyclohexyl]fluorobenzene.

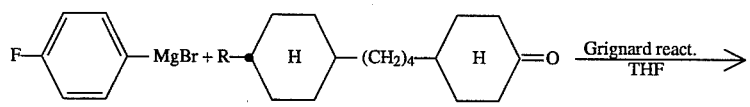

-continued

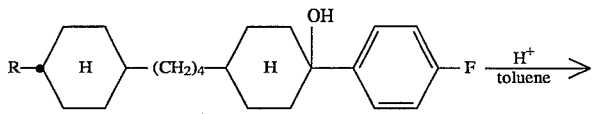

25

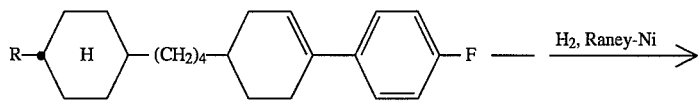

26

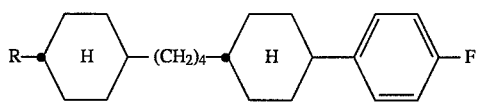

20

Further, the compound of the present invention (I-f) can be prepared according to the following process, for example.

Namely, 3,4-difluorobromobenzene is reacted with flaked Mg in THF to prepare a Grignard reagent, followed by reacting this Grignard reagent with a 4-[4-(trans-4-alkylcyclohexyl)butyl]cyclohexanone 14 to prepare an alcohol substance 27, subjecting it to dehydration reaction using an acidic ion-exchange resin for non-aqueous use as a catalyst to obtain a 4-[4-[4-(4-transalkylcyclohexyl)butyl]cyclohexen-1-yl]-1,2-difluorobenzene 28, subjecting it to catalytic reduction under pressure using Raney Ni catalyst and purifying the resulting trans substance by recrystallization to prepare the objective 4-[4-trans-[4-(4-transalkylcyclohexyl)butyl]cyclohexyl]-1,2-difluorobenzene.

alkylcyclohexyl)butyl]cyclohexanone 14 to prepare an alcohol substance 29, subjecting it to dehydration reaction using an acidic ion-exchange resin for non-aqueous use as catalyst to obtain a 4-[4-[4-(4-transalkylcyclohexyl)butyl]cyclohexen-1-yl]-1,2,6-trifluorobenzene 30, subjecting it to catalytic reduction under pressure using Raney Ni catalyst, and further purifying it by recrystallization to prepare the objective 4-[4-trans-[4-(4-transalkylcyclohexyl)butyl]cyclohexyl]-1,2,6-trifluorobenzene.

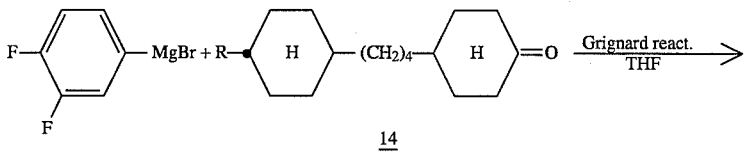

14

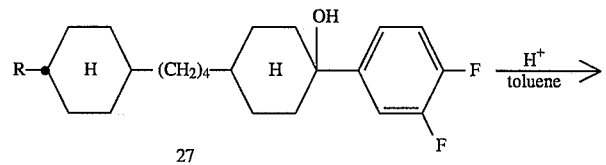

27

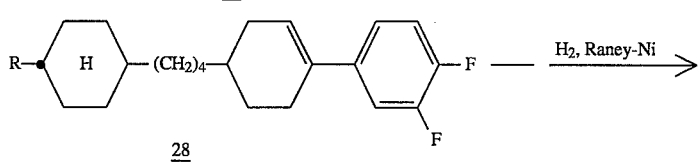

28

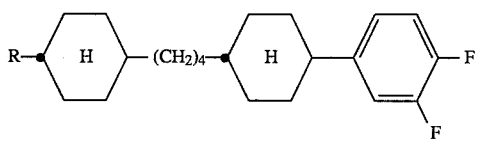

Further, the compound of the present invention (I-h) can be prepared according to the following process, for example.

Namely, 3,4,5-trifluorobromobenzene is reacted with flaked Mg in THF to prepare a Grignard reagent, followed by reacting this Grignard reagent with a 4-[4-(trans-4-

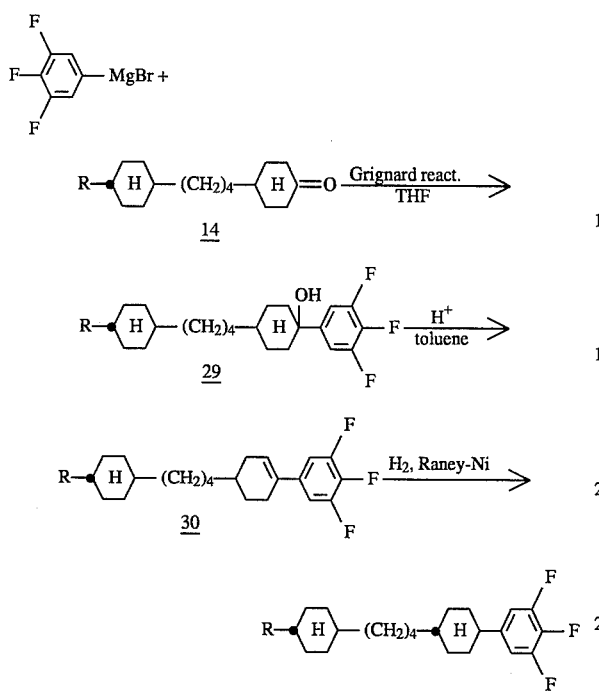

Further, the compound of the present invention (I-i) can be prepared according to the following process, for example.

Namely, a 4-alkylbromobenzene is reacted with flaked Mg in THF o prepare a Grignard reagent, followed by reacting this Grignard reagent with a 4-[4-(trans-4-alkylcyclohexyl)butyl]cyclohexanone 14 to prepare an alcohol substance 31, subjecting it to dehydration reaction using an acidic ion exchange resin for non-aqueous use as a catalyst, to obtain a 4-[4-[4-(4-transalkylcyclohexyl)butyl]cyclohexen-1-yl)alkylbenzene 32, subjecting it to catalytic reduction under pressure using Raney Ni catalyst, and purifying the resulting trans substance by recrystallization to prepare the objective 4-[4-trans-[4-(4-transalkylcyclohexyl)butyl]cyclohexyl)alkylbenzene.

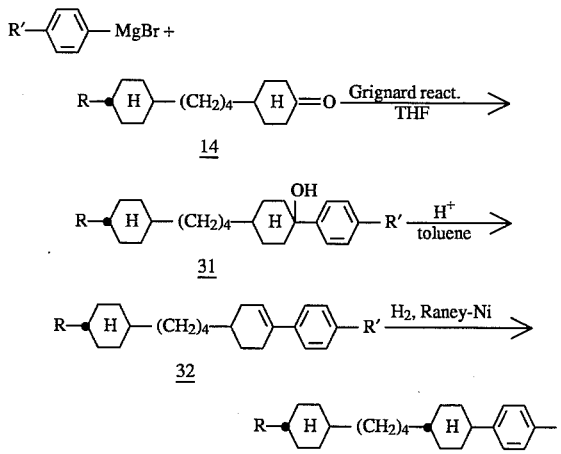

Further, the compound of the present invention (I-k), can be prepared according to the following process, for example.

Namely, 4-bromobenzotrifluoride is reacted with flaked Mg in THF to prepare a Grignard reagent, followed by reacting this Grignard reagent with a 4-[4-(trans-4-alkylcyclohexyl)butyl]cyclohexanone 14 to prepare an alcohol substance 33, subjecting it to dehydration reaction using an acidic ion exchange resin for non-aqueous use as a catalyst to obtain a 4-[4-[4-(4-transalkylcyclohexyl)butyl]cyclohexen-1-yl]benzotrifluoride 34, subjecting it to catalytic reduction under pressure using Raney-Ni catalyst, and purifying the resulting trans substance by recrystallization, to prepare the objective 4-[4-trans-[4-(4-transalkylcyclohexyl)butyl]cyclohexyl]benzotrifluoride.

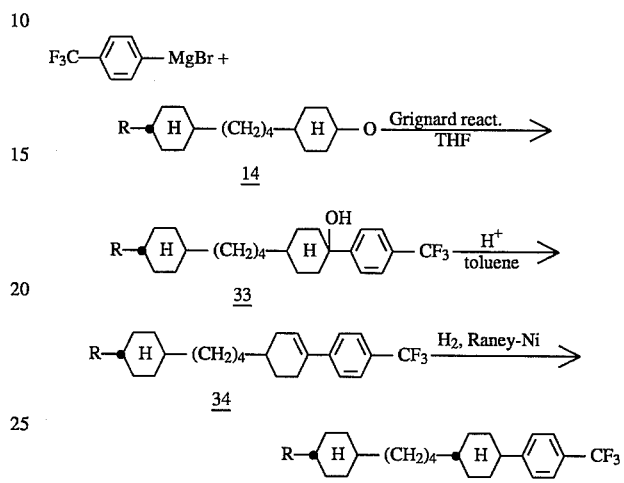

Further, the compound of the present invention (I-o) can be prepared according to the following process, for example.

Namely, 2-fluoro-4-bromobenzene is reacted with flaked Mg in THF to prepare a Grignard reagent, followed by reacting this Grignard reagent with a 4-[4-(trans-4-alkylcyclohexyl)butyl]cyclohexanone 14 to prepare an alcohol substance 35, subjecting it to dehydration reaction using an acidic ion-exchange resin as a catalyst to obtain a 4-[4-[4-(4-transalkylcyclohexyl)butyl] cyclohexen-1-yl]-2-fluorobenzene 36, subjecting it to catalytic reduction under pressure using Raney Ni catalyst and further purifying the resulting trans substance by recrystallization, to obtain a 4-[4-trans-[4-(4-transalkylcyclohexyl)butyl]cyclohexyl]-2-fluorobenzene 37, reacting this 37 with fuming nitric acid in the presence of sulfuric acid for nitration, purifying 1-nitro substance 38 by recrystallization, subjecting it to catalytic reduction under pressure in the presence of palladium-carbon catalyst to prepare an aniline derivative, a 4-[4-trans-[4-(4-transalkylcyclohexyl)butyl]cyclohexyl]-2-fluoroaniline 39, converting 39 into a sulfate using an aqueous sulfuric acid solution, reacting this sulfate with sodium nitrite under ice-cooling to obtain a diazonium salt, reacting it with potassium iodide to obtain an iodine derivative 40, purifying 40 by recrystallization, reacting it with fluorosulfonyl(difluoro)methyl acetate in the presence of cuprous iodide as a catalyst in DMF, for trifluoromethylation, and purifying the resulting product by recrystallization, to prepare the objective 4-[4-trans-[4-(4-transalkylcyclohexyl)butyl]cyclohexyl]-2-fluorobenzotrifluoride.

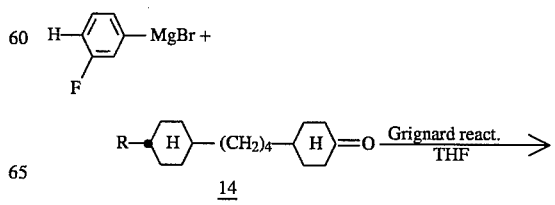

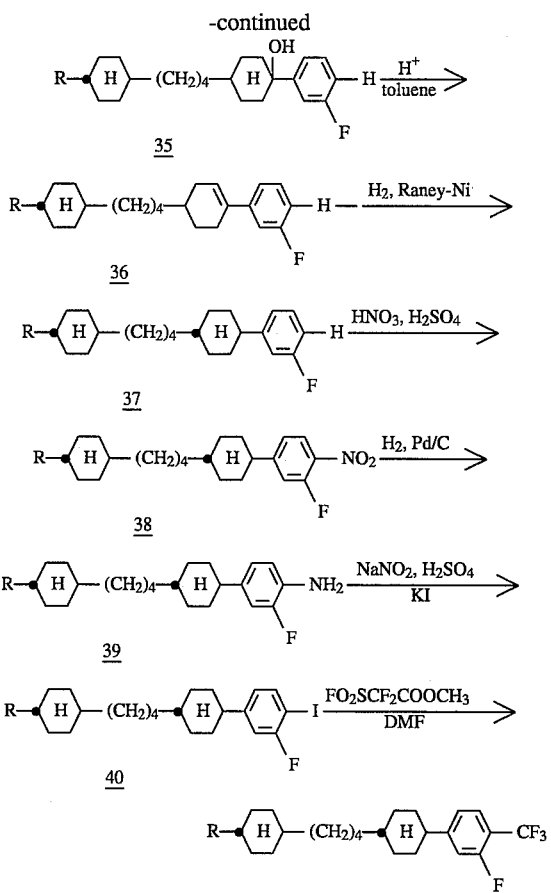

Further, the compound of the present invention (I-q) can be prepared according to the following process, for example.

Namely, 4-trifluoromethoxybromobenzene is reacted with flaked Mg in THF to prepare a Grignard reagent, followed by reacting this Grignard reagent with a 4-[4 -(trans-4-alkylcyclohexyl)butyl]cyclohexanone 14 to prepare an alcohol substance 41, subjecting it to dehydration reaction using an acidic ion exchange resin for non-aqueous use as a catalyst to obtain a 4-[4-[4-(4-transalkylcyclohexyl)butyl]cyclohexen-1-yl]trifluoromethoxybenzene 42, subjecting it to catalytic reduction under pressure using Raney Ni catalyst, and purifying the resulting trans substance by recrystallization, to prepare the objective 4-[4-trans-[4-(4-transalkylcyclohexyl)butyl]cyclohexyl] trifluoromethoxybenzene.

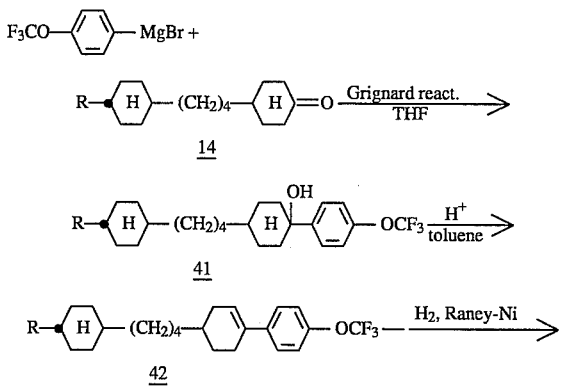

The compound of the present invention has a superior compatibility, particularly at low temperatures, with many other liquid crystalline compounds such as those of esters, Schiff's bases, biphenyls, phenylcyclohexanes, heterocyclic compounds, fluorine compounds, etc. Hence the compound can provide liquid crystal materials having improved characteristics. Further, when the compound of the present invention is added as a component of liquid crystal compositions, it is possible to broaden the usable temperature range of the liquid crystal compositions without increasing the viscosity thereof.

Preparation and use example of the compound of the present invention will be described in more detail by way of Examples.

In the following examples, the temperature properties of the mesophases are indicated by symbols C (crystal), N (nematic), I (isotropic), S (smectic), Sm (smectic), and $C_p$ represents a clearing point. $\Delta\epsilon$ represents a dielectric anisotropy calculated by the equation of $\Delta\epsilon=\epsilon_\parallel-\epsilon_\perp$, $\Delta n$ represents an optical anisotropy of a liquid crystal mixture, $\eta_{20}$ represents a viscosity at 20° C., and $V_{th}$ represents a threshold voltage.

EXAMPLE 1

Preparation of [4-[4-(trans-4-pentylcyclohexyl)butyl]cyclohexanone

The reaction step is divided into the following six steps:

1) esterification of trans-4-pentylcyclohexylacetyl chloride and reduction,
2) bromination and cyanogenation of an alcohol substance,
3) hydrolysis and esterification of a nitrile substance,
4) synthesis of acid chloride and Grignard reaction,
5) reduction and demethylation of a ketone substance, and
6) hydrogenation of the nucleus of a phenol derivative and oxidation of cyclohexanol.

The respective preparation steps will be described in more detail.

1) Ethanol (100 ml) and pyridine (50 ml) were fed into a three-neck flask provided with a stirrer, a cooling tube, a dropping funnel and a thermometer, followed by dropwise adding trans-4-pentylcyclohexylacetyl chloride with stirring at room temperature over 30 minutes, aging for one hour while keeping the temperature at 60° C. in a hot bath after completion of the dropwise addition, distilling off ethanol from the reaction solution under reduced pressure for concentration, transferring the concentrate into a separating funnel, extracting with ethyl acetate (500 ml), washing the extract solution with a saturated aqueous solution of sodium carbonate (200 ml) and water (400 ml) in this order, drying the solution over anhydrous magnesium sulfate, distilling off the solvent under reduced pressure, to obtain the reaction mixture containing an ester substance (107.9 g). This reaction mixture was used for reduction as it was. THF (250 ml) and lithium aluminum hydride (12.8 g) were fed into a three-neck flask provided with a dropping funnel, a nitrogen gas-introducing tube and a thermometer, in a nitrogen gas current, followed by cooling the mixture down to 5° C. under ice-cooling with stirring, dropwise adding a THF (120 ml) solution of the sample ester substance (107.9 g) over 90 minutes so as to keep the temperature of the system at 0° to 25° C., further aging the mixture at the same temperature for 2 hours with stirring, adding, after the reaction, ethyl acetate (70 ml), water (100 ml) and 6N hydrochloric acid aqueous solution (200 ml) in this order, transferring the reaction solution into a separating funnel, separating the THF layer, extracting the aqueous layer with diethyl ether (200 ml), mixing the THF layer with the diethyl ether layer, washing the mixture with 6NHCl aqueous solution (100 ml), water (200 ml), saturated sodium carbonate aqueous solution (100 ml) and water (200 ml) in this order, drying the mixture over anhydrous magnesium sulfate, distilling off the solvent to obtain a reaction mixture (81.8 g). The resulting alcohol substance was subjected to distillation under reduced pressure to separate a fraction of distillation temperature of 163° to 166° C./17 mmHg (69.8 g). This product is 2-(trans-4-pentylcyclohexyl)ethanol.

2) 2-(Trans-4-pentylcyclohexyl)ethanol (69.8 g) prepared in the above process of 1) and 47% hydrobromic acid (106.4 g) were fed into a three-neck flask provided with a stirrer, a thermometer and a cooling tube, followed by heating the mixture under reflux for 14.5 hours, adding the reaction solution into ice-cooled water (200 ml) to complete the reaction. The solution was transferred into a separating funnel and extracted with ethyl acetate (250 ml), followed by washing the extract layer with water (200 ml), saturated aqueous solution of sodium hydrogen carbonate (100 ml) and water (300 ml) in this order, drying over anhydrous magnesium sulfate, distilling off the solvent under reduced pressure to obtain a reaction mixture (84.0 g). The reaction mixture was distilled under reduced pressure to separate a fraction of distilling temperature of 165°–166° C./15 mmHg (60.2 g). This is 1-bromo-2-(trans-4-pentylcyclohexyl)ethane.

Sodium cyanide (59.9 g) and dimethylsulfoxide (hereinafter referred to as DMSO) (480 m) were fed into a three-neck flask provided with a cooling tube, a thermometer, a dropping funnel and a stirrer, followed by dissolving sodium cyanide on heating with stirring, dropwise adding 1-bromo-2-(trans-4-pentylcyclohexyl)ethane (245.6 g) through the dropping funnel over one hour, heating the mixture with stirring for 2 hours after completion of the dropwise addition, while keeping the temperature at 80° C., cooling down to room temperature, adding water (500 m) to complete the reaction, transferring the reaction solution into a separating funnel, extracting with toluene (1,000 ml), washing the extract layer with water (1,500 ml), drying over anhydrous magnesium sulfate, and distilling off the solvent under reduced pressure to obtain a reaction mixture (202.6 g). This is 3-(4-transpentylcyclohexyl)propionitrile.

3) An aqueous solution of KOH (KOH 158.4 g/water 60 ml) was dissolved in ethylene glycol (1,500 ml) in a three-neck flask provided with a thermometer, a cooling tube and a stirrer, followed by adding 3-(4-transpentylcyclohexyl)propionitrile (202.6 g) prepared in the step 2), heating the mixture under reflux for 8 hours, cooling the reaction solution down to room temperature after completion of the reaction, adding ice-cooled water (1,000 ml), transferring the reaction solution into a separating funnel, extracting with diethyl ether (2,000 ml), washing the extract layer with water (2,000 ml), drying over anhydrous magnesium sulfate, distilling off the solvent to obtain a reaction mixture (213.9 g). The reaction mixture was distilled under reduced pressure, to obtain a fraction of 200° to 201° C./10 mmHg (174.3 g). This is a carboxylic acid derivative, 3-(4-transpentylcyclohexyl)propionic acid. The carboxylic acid derivative, 3-(4-transpentylcyclohexyl)propionic acid (174.3 g) was added to ethanol (1,000 mR) and dissolved in a three-neck flask provided with a thermometer, a cooling tube and a stirrer, followed by adding conc. sulfuric acid (23 ml), heating the mixture under reflux for 4 hours, distilling off unreacted ethanol from the reaction system, adding the reaction residue to ice-cooled water (1,000 ml), extracting with ethyl acetate (1,000 ml), washing the extract layer with water (500 ml), a saturated aqueous solution of sodium hydrogen carbonate (500 ml) and water (1000ml) in this order, drying over anhydrous magnesium sulfate and distilling off the solvent under reduced pressure to obtain a reaction mixture (190.6 g). This is an ethyl ester derivative, 3-(4-transpentylcyclohexyl)propionic acid ethyl ester.

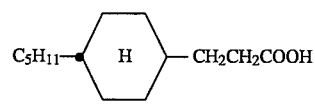

CN 56.1°–67.8° C., NI 71.3°–74.3° C.

3-(4-Transpentylcyclohexyl)propionic acid ethyl ester was subjected to repetition of the same steps as in -1) to -3) to obtain a carboxylic acid derivative, 4-(trans-4-pentylcyclohexyl)butanoic acid, having one more carbon atom increased.

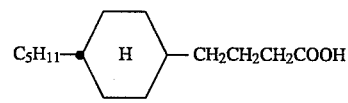

mp. 59.1°–64.1° C.

4) 4-(Trans-4-pentylcyclohexyl)butanoic acid (110.3 g) and thionyl chloride (98.5 g) were fed into an egg-plant type flask provided with a cooling tube and a thermometer, followed by heating the mixture under reflux for 3 hours, distilling off unreacted thionyl chloride under reduced pressure using an aspirator after completion of the reaction, further adding toluene (160 ml), and again distilling off toluene using an aspirator to prepare an acid chloride derivative, 4-(trans-4-pentylcyclohexyl)butylyl chloride (103.3 g). This acid chloride derivative was then used for the subsequent Grignard reaction.

Flaked Mg (13.89 g) and THF (10 ml) were fed into a three-neck flask provided with a thermometer, a cooling tube, a stirrer and a dropping funnel, followed by dropwise adding a THF (100 ml) solution of 4-methoxybromobenzene (97.1 g) at room temperature over one hour, stirring the mixture for two hours while keeping the temperature at 50° C. after completion of the dropwise addition, to prepare a Grignard reagent. A THF (200 ml) solution of 4-(trans-4-pentylcyclohexyl)butylyl chloride (103.3 g) was fed into a three-neck flask provided with a thermometer, a cooling tube, a stirrer and a dropping funnel, provided separately, cooled down to −30° C. under dry ice-alcohol refrigerant cooling, added and dissolved iron (III) acetylacetonate (2.8 g). The solution mixture was dropwise added the above-prepared Grignard reagent through the dropping funnel over one hour while keeping the temperature at −30° C. to −10° C., followed by aging the mixture at the same temperature for 3 hours after completion of the dropwise addition, and adding 6N hydrochloric acid aqueous solution (100 ml) to complete the reaction. The reaction solution was transferred into a separating funnel, followed by separating the THF layer, extracting the aqueous layer with toluene (300 ml) mixing the extract layer with the THF layer, washing the mixture with water (300 ml), a saturated aqueous solution of sodium carbonate (200 ml) and water (500 ml) in this order, drying over magnesium sulfate, distilling off the solvent under reduced pressure to obtain a reaction mixture (142.5 g). The resulting reaction mixture was subjected to silica gel column chromatography using a mixed solvent of heptane-ethyl acetate as a developing solvent, and further purifying it by recrystallization from a mixed solvent of heptane-ethyl acetate to obtain white crystals (106.4 g). The crystals was those of 4-(trans-4-pentylcyclohexyl)-1-(4-methoxyphenyl)butan-1-one.

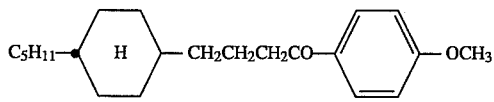

mp. 60.2°–61.3° C.

5) THF (500 ml) was fed into a three-neck flask provided with a thermometer, a cooling tube, a stirrer and a dropping funnel, followed by cooling it down to 0° C. or lower under ice-cooling, adding anhydrous aluminum chloride (154.8 g) and lithium aluminum hydride (22.0 g), dropwise adding a THF (100 ml) solution of 4-(trans-4-pentylcyclohexyl)-1-(4-methoxyphenyl)butan-1-one ( 106.4 g). over 2 hours while keeping the temperature at 0° to 5° C., stirring the mixture at the same temperature for 2 hours after completion of the dropwise addition, further stirring at room temperature for 10 hours, adding to the reaction solution, ethyl acetate (100 ml), water (100 ml) and 6N HCl aqueous solution (100 m). The reaction solution was transferred into a separating funnel after completion of the reaction, followed by separating the THF layer, extracting the aqueous layer with ethyl acetate (400 ml), mixing the extract layer with the THF layer, washing the mixture with a saturated aqueous solution of sodium carbonate (200 ml) and water (500 ml), drying over anhydrous magnesium sulfate, and distilling off the solvent under reduced pressure to obtain a reaction mixture (113.0 g). This is 1-(4-transpentylcyclohexyl)-4-(4-methoxyphenyl)butane. The reaction mixture was reacted with boron tribromide as it was. Methylene chloride (700 ml) was fed into a three-neck flask provided with a thermometer, a cooling tube, a stirrer and a dropping funnel, followed by cooling it down to –60° C. with dry ice-acetone refrigerant, adding boron tribromide (107.5 g), after completion of the addition, gradually dropwise adding a methylene chloride (500 ml) solution of 1-(4-transpentylcyclohexyl)-4-(4-methoxyphenyl)butane (113.0 g) over 2 hours while keeping the temperature at –60° to –40° C., after the dropwise addition, further stirring the mixture at the same temperature for one hour, gradually elevating the temperature up to room temperature over one hour, further adding water (500 ml) to complete the reaction. The reaction solution was transferred into a separating funnel, followed by separating the methylene chloride layer, washing with water (1,000 ml), drying over anhydrous magnesium sulfate, and distilling off the solvent, to obtain a reaction mixture (82.9 g). The reaction mixture was recrystallized from a mixed solvent of heptaneethanol to obtain white crystals (57.0 g). The crystals are those of a phenol derivative, 1-(4-transpentylcyclohexyl)-4-(4-hydroxyphenyl)butane.

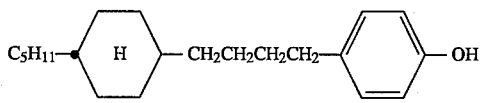

mp. 84.8°–86.0° C.

6) The above sample, 1-(4-transpentylcyclohexyl)-4-(4-hydroxyphenyl)butane (57 g) was dissolved in cyclohexane (200 ml), followed by placing the solution in an autoclave, subjecting it to catalytic hydrogenation using a palladium supported on barium sulfate as a catalyst under a hydrogen pressure of 25 Kg/cm$^2$ for 2 hours, filtering off the catalyst from the reaction solution after completion of the reaction, and distilling off the solvent under reduced pressure to obtain a reaction mixture (60.3 g). This is 1-(4-transpentylcyclohexyl)-4-(4-hydroxycyclohexyl)butane. The reaction mixture was subjected to oxidation reaction with sodium hypochlorite, without purifying the reaction mixture, as it was. In an egg-plant type flask provided with a thermometer and a dropping funnel, the sample, 1-(4-transpentylcyclohexyl)-4-(4-hydroxycyclohexyl)butane (60.3 g) was dissolved in chloroform (200 ml), followed by dropwise adding a 28% aqueous solution of sodium hypochlorite (60 ml) at room temperature over 20 minutes with stirring by means of a magnetic stirrer, further stirring the mixture at the same temperature for 15 hours after completion of the dropwise addition, and adding water (500 ml) to complete the reaction. The reaction solution was transferred into a separating funnel to separate the chloroform layer, followed by extracting the aqueous layer with chloroform (200 ml), mixing the chloroform layers, washing with 2N aqueous solution of NaOH (100 ml) and water (1,600 ml), drying over anhydrous magnesium sulfate, and distilling off the solvent under reduced pressure, to obtain a reaction mixture (53.6 g). The reaction mixture was purified according to silica gel column chromatography using toluene as a developing solvent, to obtain white crystals (47.9 g). The crystals are those of 4-[4-(trans-4-pentylcyclohexyl)butyl]cyclohexanone.

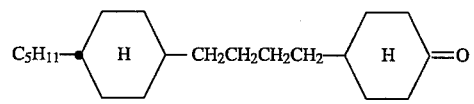

mp. 34.3°–51.0° C.

Using trans-4-alkylcyclohexylacetyl chlorides each having different alkyl groups in place of trans-4-pentylcyclohexylacetyl chloride, the following 4-[4-(trans-4-alkylcyclohexyl)butyl]cyclohexanone according to the above preparation process can be prepared.

4-[4-(trans-4-ethylcyclohexyl)butyl]cyclohexanone

4-[4-(trans-4-propylcyclohexyl)butyl]cyclohexanone
 m.p. 40.6°–43.6° C.

4-[4-(trans-4-butylcyclohexyl)butyl]cyclohexanone

4-[4-(trans-4-hexylcyclohexyl)butyl]cyclohexanone

4-[4-(trans-4-heptylcyclohexyl)butyl]cyclohexanone

4-[4-(trans-4-octylcyclohexyl)butyl]cyclohexanone

4-[4-(trans-4-nonylcyclohexyl)butyl]cyclohexanone

EXAMPLE 2

Preparation of 4-[4-trans-[4-(4-transpentylcyclohexyl)butyl]cyclohexyl]benzonitrile (a compound of the formula (I) wherein R=n-C$_5$H$_{11}$, X$_1$=X$_3$=H and X$_2$=CN)

The reaction step is divided into the following four steps:
1) Grignard reaction;
2) dehydration reaction of alcohol;
3) catalytic hydrogenation of cyclohexene derivative; and
4) cyanogenation.

The preparation steps will be described in more detail.

1) Preparation of Grignard reagent was carried out in a conventional manner. Mg (1.2 g) and THF (3 ml) were placed in a three-neck flask provided with a thermometer, a cooling tube and a dropping funnel, followed by dropwise adding and reacting a THF solution (10 ml) of bromobenzene (7.3 g) at room temperature over 30 minutes with stirring by a magnetic stirrer, aging with stirring for one hour while keeping the temperature at 50° C. in a hot bath, after completion of the dropwise addition, to prepare a Grignard reagent. A THF (25 ml) solution of 4-[4-(trans-4-pentylcyclohexyl)butyl]cyclohexanone (11 g) was dropwise added to the Grignard reagent over 30 minutes so as to keep the temperature inside the system at 40° to 60° C., after the aging, followed by aging at the same temperature for 4 hours, cooling with ice after the aging, adding 6N HC aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over magnesium sulfate, and distilling off the solvent under reduced pressure to obtain a reaction mixture (12.5 g). This is a mixture containing 4-[4-[4-(4-transpentylcyclohexyl)butyl]-1-hydroxycyclohexyl]benzene. The thus obtained reaction mixture was used in the subsequent dehydration reaction step, as it was.

2) In a three-neck flask provided with a drain tube, a cooling tube and a stirrer, the mixture containing 4-[4-[4-(4-transpentylcyclohexyl)butyl]-1-hydroxycyclohexyl]benzene (12.5 g) was dissolved in toluene (63 ml), followed by adding an acidic ion exchange resin for non-aqueous use as a catalyst (0.6 g), heating the mixture under reflux with stirring for one hour, filtering off the catalyst from the reaction solution, distilling off the solvent under reduced pressure and concentrating to obtain a reaction mixture (10.9 g). The thus obtained reaction mixture was purified according to silica gel-filled column chromatography, followed by recrystallizing from a mixed solvent of heptane-ethyl acetate to obtain pale yellow crystals (8.2 g). The crystals are those of 4-[4-[4-(4-transpentylcyclohexyl)butyl] cyclohexen-1-yl]benzene.

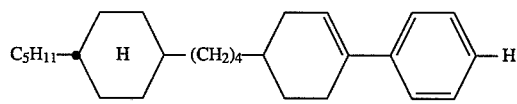

CN 50.1°–55.4° C., NI 75.5°–76.8° C.

3) In an egg-plant type flask, 4-[4-[4-(4-transpentylcyclohexyl)butyl]cyclohexen-1-yl]benzene (8.2 g) was dissolved in ethyl acetate (60 ml), followed by adding a developing Raney nickel catalyst (4.0 g), subjecting the solution to catalytic hydrogenation under a hydrogen pressure of 5 to 10 Kg/cm$^2$ at room temperature for 20 hours, filtering off the catalyst after completion of the reaction, distilling off the solvent under reduced pressure to obtain a reaction mixture (7.5 g). The reaction mixture was isomerized in a conventional manner to obtain an isomerized reaction mixture (6.8 g), followed by recrystallizing the reaction mixture from a mixed solvent of heptane-ethyl acetate, for purification of a trans substance, to obtain white crystals (3.4 g). The crystals are those of 4-[4-[4-trans-(4-transpentylcyclohexyl)butyl]cyclohexyl]benzene.

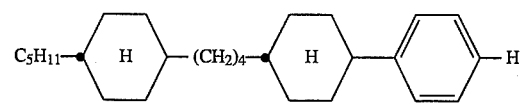

CS 59.1°–60.1° C., SN 73.2°–76.8° C. NI 78.9°–79.4° C.

4) In a three-neck flask provided with a thermometer, a cooling tube and a dropping funnel, 4-[4-[4-trans-(4-transpentylcyclohexyl)butyl]cyclohexyl]benzene (3.4 g) was dissolved in dichloromethane (30 ml), followed by cooling the solution down to −10° C. under ice-cooling, adding anhydrous aluminum chloride (3.7 g), dropwise adding oxalyl chloride (3.5 g) with stirring by means of a magnetic stirrer for 5 minutes while keeping the temperature at −10° to −5° C., stirring at the same temperature for one hour after completion of the dropwise addition, returning the temperature to room temperature, further stirring for 3 hours, adding water (50 ml) to complete the reaction. The reaction solution was transferred into a separating funnel to separate the dichloromethane layer, followed by extracting the aqueous layer with dichloromethane (40 ml), mixing the extract layer with the separated dichloromethane layer, washing with water (50 ml), a saturated aqueous solution of sodium carbonate (50 ml) and water (100 ml) in this order, drying over anhydrous magnesium sulfate, distilling off the solvent under reduced pressure and concentrating to obtain a reaction mixture (3.5 g). This is that of 4-[4-[4-trans-(4-transpentylcyclohexyl)butyl]cyclohexyl]benzoyl chloride. The reaction mixture was dissolved in 1,4-dioxane (3 ml), as it was, followed by adding the solution to 25% -aqueous ammonia (20 ml), reacting them, filtering off the resulting solids, washing with water (100 ml) and drying to obtain pale yellow crystals (3.9 g). The crystals are those of an acid amide derivative, 4-[4-[4-trans-(4-transpentylcyclohexyl)butyl]cyclohexyl]benzamide. The dried 4-[4-[4-trans-(4-transpentylcyclohexyl)butyl]cyclohexyl]benzamide (3.5 g) was placed in a three-neck flask provided with a thermometer, a stirrer, a cooling tube and a dropping funnel, followed by dissolving it in a solution of pyridine/toluene (1:1) (30 ml) on heating with stirring, allowing the solution to cool down to room temperature, dropwise adding benzenesulfonyl chloride (2.3 g) at room temperature over 5 minutes, further heating the mixture under reflux for 4 hours after completion of the dropwise addition, allowing to cool down to room temperature, adding the reaction solution into an ice-cooled water (50 ml) to complete the reaction. The reaction mixture was transferred into a separating funnel to separate the organic layer, followed by extracting the aqueous layer with toluene (50 ml), mixing the organic layers with the extract, washing with 6N HCl aqueous solution (20 ml), water (50 ml), a saturated aqueous solution of sodium carbonate (40 ml) and water (100 ml) in this order, drying over anhydrous magnesium sulfate, distilling off the solvent under reduced pressure, concentrating to obtain a reaction mixture (2.9 g). The reaction mixture was purified according to silica gel-filled column chromatography using a mixed solvent of heptane-ethyl acetate as a developing solvent, followed by repeatedly recrystallizing from a mixed solvent of heptane-ethyl acetate to obtain white crystals (1.2 g). The crystals are those of the objective 4-[4-trans-[4-(4-transpentylcyclohexyl)butyl]cyclohexyl]benzonitrile.

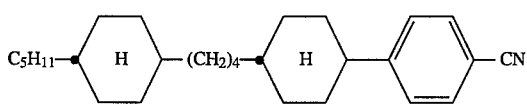

CN 85.4°–88.0° C., NI 150.9°–154.2° C.

Using 4-[4-[trans-4-alkylcyclohexyl)butyl]cyclohexanones, each having different alkyl groups in place of 4-[4-[trans-4-pentylcyclohexyl)butyl]cyclohexanone, the following 4-[4-trans-[4-(4-transalkylcyclohexyl)butyl]cyclohexyl]benzonitriles can be prepared according to the above preparation process:

4-[4-trans-[4-(4-transethylcyclohexyl)butyl] cyclohexyl] benzonitrile

4-[4-trans-[4-(4-transpropylcyclohexyl)butyl]cyclohexyl] benzontrile

4-[4-trans-[4-(4-transbutylcyclohexyl)butyl] cyclohexyl] benzontrile

4-[4-trans-[4-(4-transhexylcyclohexyl)butyl]cyclohexyl] benzonitrile

4-[4-trans-[4-(4-transheptylcyclohexyl)butyl]cyclohexyl] benzonitrile

4-[4-trans-[4-(4-transoctylcyclohexyl)butyl]cyclohexyl] benzonitrile

4-[4-trans-[4-(4-transnonylcyclohexyl)butyl] cyclohexyl] benzontrile

EXAMPLE 3

Preparation of 4-[4-trans-[4-(4-transpentylcyclohexyl)butyl]cyclohexyl]-2-fluorobenzonitrile (a compound of the formula (I) wherein R=n-$C_5H_{11}$, $X_1$=F, $X_3$=H and $X_2$=CN)

The reaction step is divided into the following four steps:

1) Grignard reaction;

2) dehydration reaction of alcohol;

3) catalytic hydrogenation of cyclohexene derivative; and 4) cyanogenation. The preparation steps will be described in more detail.

1) Preparation of Grignard reagent was carried out in a conventional manner. Mg (2.8 g) and THF (10 ml) were placed in a three-neck flask provided with a thermometer, a cooling tube and a dropping funnel, followed by dropwise adding and reacting a THF solution (40 ml) of 3-fluorobromobenzene (20.4 g) at room temperature over 50 minutes with stirring by a magnetic stirrer, aging with stirring for one hour while keeping the temperature at 50° C. in a hot bath, after completion of the dropwise addition, to prepare a Grignard reagent. A THF solution (50 ml) of 4-[4-(trans-4-pentylcyclohexyl)butyl]cyclohexanone (25 g) was dropwise added to the Grignard reagent over 45 minutes so as to keep the temperature inside the system at 40° to 60° C., after the aging, followed by aging at the same temperature for 4 hours, cooling with ice after the aging, adding 6N HCl aqueous solution (100 ml) to complete the reaction. The reaction solution was transferred into a separating funnel, followed by washing with water (200 ml), a saturated aqueous solution of sodium carbonate (200 ml) and water (400 ml) in this order, drying over magnesium sulfate, and distilling off the solvent under reduced pressure to obtain a reaction mixture (31.5 g). This is a mixture containing 4-[4-[4-(4-transpentylcyclohexyl)butyl]-1-hydroxycyclohexyl]-2-fluorobenzene. The thus obtained reaction mixture was used in the subsequent dehydration reaction step, as it was.

2) In a three-neck flask provided with a drain tube, a cooling tube and a stirrer, the mixture containing 4-[4-[4-(4-transpentylcyclohexyl)butyl]-1-hydroxycyclohexyl]-2-fluorobenzene (31.5 g) was dissolved in toluene (160 ml), followed by adding an acidic ion exchange resin for non-aqueous use as a catalyst (1.6 g), heating the mixture under reflux with stirring for one hour, filtering off the catalyst from the reaction solution, distilling off the solvent under reduced pressure and concentrating to obtain a reaction mixture (30.3 g). The thus obtained reaction mixture was purified according to silica gel-filled column chromatography, followed by recrystallizing from a mixed solvent of heptane-ethylacetate to obtain pale yellow crystals (26.8 g). The crystals are those of 4-[4-[4-(4-transpentylcyclohexyl)butyl]cyclohexene-1-yl]-2-fluorobenzene.

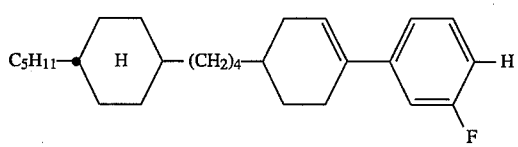

3) In an egg-plant type flask, 4-[4-[4-(4-transpentylcyclohexyl)butyl]cyclohexene-1-yl]-2-fluorobenzene (26.8 g) was dissolved in ethylacetate (150 ml), followed by adding a developing Raney nickel catalyst (10.0 g), subjecting the solution to catalytic hydrogenation under a hydrogen pressure of 5 to 10 kg/cm$^2$ at room temperature for 20 hours, filtering off the catalyst after completion of the reaction, distilling off the solvent under reduced pressure to obtain a reaction mixture (26.4 g). The reaction mixture was recrystallized from a mixed solvent of heptane-ethylacetate, for purification of a trans substance, to obtain white crystals (12.7 g). The crystals are those of 4-[4-[4-trans-(4-transpentylcyclohexyl)butyl] cyclohexyl]-2-flourobenzene.

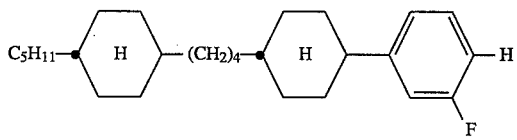

CN 49.2°–56.5° C., NI 68.2°–69.8° C.

4) In a three-neck flask provided with a thermometer, a cooling tube and a dropping funnel, 4-[4-[4-trans-(4-transpentylcyclohexyl)butyl]cyclohexyl]-2-fluorobenzene (5.0 9) was dissolved in dichloromethane (50 ml), followed by cooling the solution down to −10° C. under ice-cooling, adding anhydrous aluminum chloride (5.2 9), dropwise adding oxalyl chloride (4.9 9) with stirring by means of a magnetic stirrer over 30 minutes while keeping the temperature at −10° to −5° C., stirring at the same temperature for one hour after completion of the dropwise addition, returning the temperature to room temperature, further stirring for 3 hours, adding water (50 ml) to complete the reaction. The reaction solution was transferred into a separating funnel, to separate the dichloromethane layer, followed by extracting the aqueous layer with dichloromethane (50 ml), mixing the extract layer with the separated dichloromethane layer, washing water (100 ml), a saturated aqueous solution of sodium carbonate (50 ml) and water (150 ml) in this order, drying over anhydrous magnesium sulfate, distilling off the solvent under reduced pressure and concentrating to obtain a reaction mixture (5.5 g). This is that of 4-[4-[4-trans-(4-transpentylcyclohexyl)butyl]cyclohexyl]-2-fluorobenzoyl chloride. The reaction mixture was dissolved in 1,4-dioxane (5 ml), as it was, followed by adding the solution to 25%-aqueous ammonia (20 ml), reacting them, filtering off the resulting solids, washing with water (100 ml) and drying to obtain pale yellow crystals (4.9 g). The crystals are those of an acid amide derivative, 4-[4-[4-trans-(4-transpentylcyclohexyl)butyl]cyclohexyl]-2-fluorobenzamide. The dried 4-[4-[4-trans-(4-transpentylcyclohexyl)butyl]cyclohexyl]-2-fluorobenzamide (4.5 g) was placed in a three-neck flask provided with a thermometer, a stirrer, a cooling tube and a dropping funnel, followed by dissolving it in a solution of pyridine/toluene (1:1) (50 ml) on heating with stirring, allowing the solution to cool down to room temperature, dropwise adding benzenesulfonyl chloride (3.0 g) at room temperature over 3 minutes, further heating the mixture under reflux for 4 hours after completion of the dropwise addition, allowing to cool down to room temperature, adding the reaction solution into an ice-cooled water (50 ml) to complete the reaction. The reaction mixture was transferred into a separating funnel to separate the organic layer, followed by extracting the aqueous layer with toluene (50 ml), mixing the organic layers with the extract, washing with 6N HCl aqueous solution (30 ml), water (50 ml), a saturated aqueous solution of sodium carbonate (50 ml) and water (200 ml) in this order, drying over anhydrous magnesium sulfate, distilling off the solvent under reduced pressure; concentrating to obtain a reaction mixture (4.3 g). The reaction mixture was purified according to silica gel-filled column chromatography using a mixed solvent of heptane-ethylacetate as a developing solvent, followed by repeatedly recrystallizing from a mixed solvent of heptane-ethylacetate to obtain white crystals (1.6 g). The crystals are those of the objective 4-[4-trans-[4-(4-transpentylcyclohexyl)butyl]cyclohexyl]-2-fluorobenzonitrile.

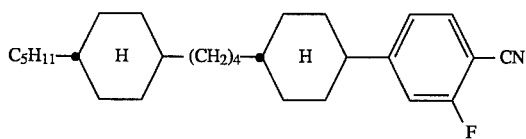

CN 69.5°–70.9° C., NI 124.7°–125.9° C.

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]-2-fluorobenzonitriles can be prepared according to the above preparation process:

4-[4-trans-[4-(4-transethylcyclohexyl)butyl]cyclohexyl]-2-fluorobenzonitrile

4-[4-trans-[4-(4-transpropylcyclohexyl)butyl]cyclohexyl]-2-fluorobenzonitrile

4-[4-trans-[4-(4-transbutylcyclohexyl)butyl]cyclohexyl]-2-fluorobenzonitrile

4-[4-trans-[4-(4-transhexylcyclohexyl)butyl]cyclohexyl]-2-fluorobenzonitrile

4-[4-trans-[4-(4-transheptylcyclohexyl)butyl]cyclohexyl]-2-fluorobenzonitrile

4-[4-trans-[4-(4-transoctylcyclohexyl)butyl]cyclohexyl]-2-fluorobenzonitrile

4-[4-trans-[4-(4-transnonylcyclohexyl)butyl]cyclohexyl]-2-fluorobenzontrile

EXAMPLE 4

Preparation of 4-[4-trans-[4-(4-transpentylcyclohexyl)butyl]cyclohexyl]fluorobenzene (a compound of the formula (I) wherein R=n-$C_3H_7$, $X_1=X_3=H$ and $X_2=F$)

The reaction step is divided into the following three steps:
1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.1 g) and THF (3 ml) were placed in a three-neck flask provided with a thermometer, a cooling tube and a dropping funnel, followed by dropwise adding and reacting a THF solution (15 ml) of 4-fluorobromobenzene (7.4 g) at room temperature over 30 minutes with stirring by a magnetic stirrer, aging with stirring for 2.5 hours while keeping the temperature at 50° C. in a hot bath, after completion of the dropwise addition, to prepare a Grignard reagent. A THF solution (25 ml) of 4-[4-(trans-4-propylcyclohexyl)butyl]cyclohexanone (9 g) was dropwise added to the Grignard reagent over 30 minutes so as to keep the temperature inside the system at 40° to 60° C., after the aging, followed by aging at the same temperature for 4 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over magnesium sulfate, and distilling off the solvent under reduced pressure to obtain a reaction mixture (9.4 g). The obtained reaction mixture was recrystallized from a mixed solvent of heptane and ethylacetate to obtain yellow brown crystals (7.2 g). This is 4-[4-[4-(4-transpropylcyclohexyl)butyl]-1-hydroxycyclohexyl]fluorobenzene.

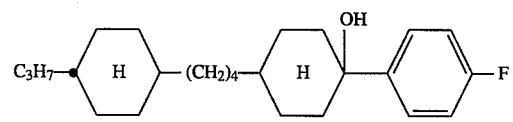

m.p. 63.3°–69.8° C.

2) In a three-neck flask provided with a thermometer, a cooling tube and a stirrer, 4-[4-[4-(4-transpropylcyclohexyl)butyl]-1-hydroxycyclohexyl]fluorobenzene (7.2 9) was dissolved in toluene (20 ml), followed by adding an acidic ion exchange resin for non-aqueous use as a catalyst (0.3 ), heating the mixture under reflux with stirring for one hour, filtering off the catalyst from the reaction solution, distilling off the solvent under reduced pressure and concentrating to obtain a reaction mixture (6.6 g). The thus obtained reaction mixture was purified according to silica gel-filled column chromatography, followed by recrystallizing from a mixed solvent of heptane-ethylacetate to obtain pale yellow crystals (5.3 g). The crystals are those of 4-[4-[4-(4-transpropylcyclohexyl)butyl]cyclohexene-1-yl]fluorobenzene.

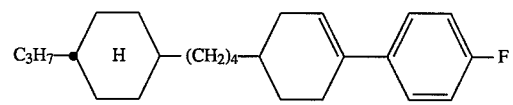

CN 50.2°–61.0° C., NI 86.0°–97.3° C.

3) In an egg-plant type flask, 4-[4-[4-(4-transpropylcyclohexyl)butyl]cyclohexene-1-yl] fluorobenzene (5.3 g) was dissolved in ethylacetate (70 ml), followed by adding a developing Raney nickel catalyst (4.5 g), subjecting the solution to catalytic hydrogenation under a hydrogen pressure of 5 to 10 kg/cm² at room temperature for 20 hours, filtering off the catalyst after completion of the reaction, distilling off the solvent under reduced pressure to obtain a reaction mixture (5.1 g). The reaction mixture was isomerized in a conventional manner to obtain an isomerized reaction mixture (4.5 g), followed by recrystallizing the reaction mixture from a mixed solvent of heptane-ethylacetate, for purification of a trans substance, to obtain white crystals (1.2 g). The crystals are those of 4-[4-[4-trans-(4-transpropylcyclohexyl)butyl]cyclohexyl]fluorobenzene.

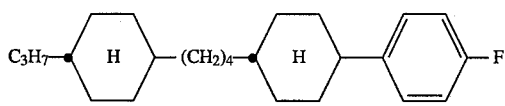

CN 63.6°–69.1° C., NI 102.3°–105.1° C.

Using 4-[4-(trans-4-alkylcyclohexyl)butyl]cyclohexanones, each having different alkyl groups in place of 4-[4-(trans-4-propylcyclohexyl)butyl]cyclohexanone, the following 4-[4-trans-[4-(4-transalkylcyclohexyl)butyl]cyclohexyl]fluorobenzenes can be prepared according to the above preparation process:

4-[4-trans-[4-(4-transethylcyclohexyl)butyl]cyclohexyl] fluorobenzene

4-[4-trans-[4-(4-transbutylcyclohexyl)butyl]cyclohexyl] fluorobenzene

4-[4-trans-[4-(4-transpentylcyclohexyl)butyl]cyclohexyl] fluorobenzene

4-[4-trans-[4-(4-transhexylcyclohexyl)butyl]cyclohexyl] fluorobenzene

4-[4-trans-[4-(4-transheptylcyclohexyl)butyl]cyclohexyl] fluorobenzene

4-[4-trans-[4-(4-transoctylcyclohexyl)butyl]cyclohexyl] fluorobenzene

4-[4-trans-[4-(4-transnonylcyclohexyl)butyl]cyclohexyl] fluorobenzene

EXAMPLE 5

Preparation of 4-[4-trans-[4-(4-transpentylcyclohexyl)butyl]cyclohexyl]-1,2-difluorobenzene (a compound of the formula (I) wherein R=n-$C_5H_{11}$, $X_1$=F, $X_3$=H and $X_2$=F)

The reaction step is divided into the following three steps:

1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.1 g) and THF (3 ml) were placed in a three-neck flask provided with a thermometer, a cooling tube and a dropping funnel, followed by dropwise adding and reacting a THF solution (25 ml) of 3,4-difluorobromobenzene (8.2 g) at room temperature over 30 minutes with stirring by a magnetic stirrer, aging with stirring for 3.5 hours while keeping the temperature at 50° C. in a hot bath, after completion of the dropwise addition, to prepare a Grignard reagent. A THF solution (25 ml) of 4-[4-(trans-4-pentylcyclohexyl)butyl]cyclohexanone (10 g) was dropwise added to the Grignard reagent over 30 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over magnesium sulfate, and distilling off the solvent under reduced pressure to obtain a reaction mixture (13.8 g). The obtained reaction mixture was recrystallized from a mixed solvent of heptane-ethylacetate to obtain yellow brown crystals (9.8 g). This is 4-[4-[4-(4-transpentylcyclohexyl)butyl]-1-hydroxycyclohexyl]-1,2-difluorobenzene.

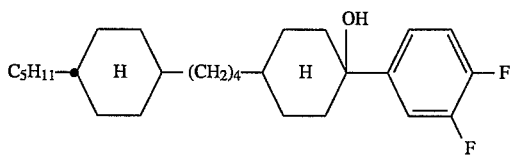

m.p. 54.7°–59.0° C.

2) In a three-neck flask provided with a drain tube, a cooling tube and a stirrer, the mixture containing 4-4-[4-(4-transpentylcyclohexyl)butyl]-1-hydroxycyclohexyl]-1,2-difluorobenzene (9.8 g) was dissolved in toluene (70 ml), followed by adding an acidic ion exchange resin for non-aqueous use as a catalyst (0.7 g), heating the mixture under reflux with stirring for one hour, filtering off the catalyst from the reaction solution, distilling off the solvent under reduced pressure and concentrating to obtain a reaction mixture (8.5 g). The thus obtained reaction mixture was purified according to silica gel-filled column chromatography, followed by recrystallizing from a mixed solvent of heptane-ethylacetate to obtain pale yellow crystals (7.1 g). The crystals are those of 4-[4-[4-(4-transpentylcyclohexyl)butyl]cyclohexen-1-yl]-1,2-difluorobenzene.

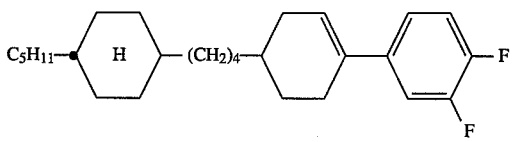

CN 37.5°–40.5° C., NI 73.6°–80.5° C.

3) In an egg-plant type flask, 4-[4-[4-(4-transpentylcyclohexyl)butyl]cyclohexen-1-yl]-1,2-difluorobenzene (7.1 g) was dissolved in ethylacetate (60 ml), followed by adding a developing Raney nickel catalyst (4.0 g), subjecting the solution to catalytic hydrogenation under a hydrogen pressure of 5 to 10 kg/cm² at room temperature for 20 hours, filtering off the catalyst after completion of the reaction, distilling off the solvent under reduced pressure to obtain a reaction mixture (7.3 g). The reaction mixture was isomerized in a conventional manner to obtain an isomerized reaction mixture (6.5 g), followed by recrystallizing the reaction mixture from a mixed solvent of heptane-ethylacetate, for purification of a trans substance, to obtain white crystals (1.5 g). The crystals are those of 4-[4-[4-trans-(4-transpentylcyclohexyl)butyl]cyclohexyl]-1,2-difluorobenzene.

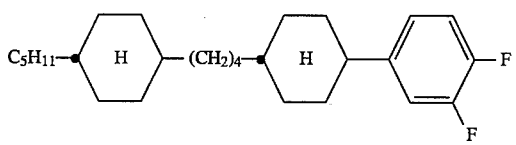

CN 50.6°–55.8° C., NI 85.8°–87.7° C.

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]-1,2-difluorobenzenes can be prepared according to the above preparation process:

4-[4-trans-[4-(4-transethylcyclohexyl)butyl]cyclohexyl]-1,2-difluorobenzene

4-[4-trans-[4-(4-transpropylcyclohexyl)butyl]cyclohexyl]-1,2-difluorobenzene

4-[4-trans-[4-(4-transbutylcyclohexyl)butyl]cyclohexyl]-1,2-difluorobenzene

4-[4-trans-[4-(4-transhexylcyclohexyl)butyl]cyclohexyl]-1,2-difluorobenzene

4-[4-trans-[4-(4-transheptylcyclohexyl)butyl]cyclohexyl]-1,2-diflurobenzene

4-[4-trans-[4-(4-transoctylcyclohexyl)butyl]cyclohexyl]-1,2-difluorobenzene

4-[4-trans-[4-(4-transnonylcyclohexyl)butyl]cyclohexyl]-1,2-difluorobenzene

EXAMPLE 6

Preparation of 4-[4-trans-[4-(4-transpentylcyclohexyl)butyl]cyclohexyl]-1,2,6-trifluorobenzene (a compound of the formula (I) wherein R=n-$C_5H_{11}$ and $X_1=X_2=X_3=F$)

The reaction step is divided into the following three steps:

1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (0.9 g) and THF (3 ml) were placed in a three-neck flask provided with a thermometer, a cooling tube and a dropping funnel, followed by dropwise adding and reacting a THF solution (20 ml) of 3,4,5-trifluorobromobenzene (7.4 g) at room temperature over 30 minutes with stirring by a magnetic stirrer, aging with stirring for 3.0 hours while keeping the temperature at 50° C. in a hot bath, after completion of the dropwise addition, to prepare a Grignard reagent. A THF solution (25 ml) of 4-[4-(trans-4-pentylcyclohexyl)butyl]cyclohexanone (10 g) was dropwise added to the Grignard reagent over 30 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over magnesium sulfate, and distilling off the solvent under reduced pressure to obtain a reaction mixture (13.5 g). This is a mixture containing 4-[4-[4-(4-transpentylcyclohexyl)butyl]-1-hydroxycyclohexyl]-1,2,6-trifluorobenzene. The thus obtained reaction mixture was used in the subsequent dehydration reaction step, as it was.

2) In a three-neck flask provided with a drain tube, a cooling tube and a stirrer, the mixture containing 4-[4-[4-(4-transpentylcyclohexyl)butyl]-1-hydroxycyclohexyl]-1,2,6-trifluorobenzene (13.5 g) was dissolved in toluene (70 ml), followed by adding an acidic ion exchange resin for non-aqueous use as a catalyst (0.7 g), heating the mixture under reflux with stirring for one hour, filtering off the catalyst from the reaction solution, distilling off the solvent under reduced pressure and concentrating to obtain a reaction mixture (10.6 g). The thus obtained reaction mixture was purified according to silica gel-filled column chromatography, followed by recrystallizing from a mixed solvent of heptane-ethylacetate to obtain white crystals (8.5 g). The crystals are those of 4-[4-[4-(4-transpentylcyclohexyl)butyl]cyclohexen-1-yl]-1,2,6-trifluorbenzene.

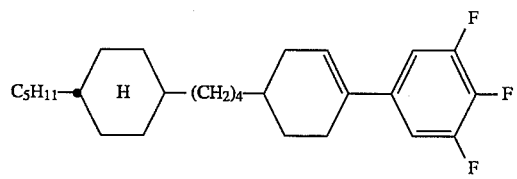

CN 47.2°–50.8° C., NI 66.6°–67.7° C.

3) In an egg-plant type flask, 4-[4-[4-(4-transpentylcyclohexyl)butyl]cyclohexen-1-yl]-1,2,6-trifluorobenzene (8.5 g) was dissolved in ethylacetate (60 ml), followed by adding a developing Raney nickel catalyst (4.0 g), subjecting the solution to catalytic hydrogenation under a hydrogen pressure of 5 to 10 kg/cm² at room temperature for 20 hours, filtering off the catalyst after completion of the reaction, distilling off the solvent under reduced pressure to obtain a reaction mixture (8.3 g). The trans substance of the reaction mixture was purified and recrystallized from a mixed solvent of heptane-ethylacetate, to obtain white crystals (2.0 g). The crystals are those of 4-[4-[4-trans-(4-transpentylcyclohexyl)butyl]cyclohexyl]-1,2,6-trifluorobenzene.

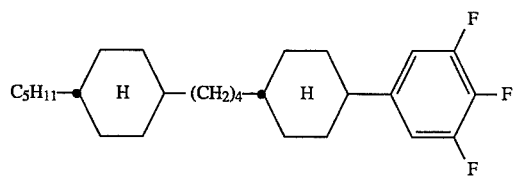

CN 54.0°–55.7° C., NI 73.2°–73.9° C.

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]-1,2,6-trifluorobenzenes can be prepared according to the above preparation process:

4-[4-trans-[4-(4-transethylcyclohexyl)butyl]cyclohexyl]-1,2,6-trifluorobenzene

4-[4-trans-[4-(4-transpropylcyclohexyl)butyl]cyclohexyl]-1,2,6-trifluorobenzene

4-[4-trans-[4-(4-transbutylcyclohexyl)butyl]cyclohexyl]-1,2,6-trifluorobenzene

4-[4-trans-[4-(4-transhexylcyclohexyl)butyl]cyclohexyl]-1,2,6-trifluorobenzene

4-[4-trans-[4-(4-transheptylcyclohexyl)butyl]cyclohexyl]-1,2,6-trifluorobenzene

4-[4-trans-[4-(4-transoctylcyclohexyl)butyl]cyclohexyl]-

1,2,6-trifluorobenzene
4-[4-trans-[4-(4-transnonylcyclohexyl)butyl]cyclohexyl]-1,2,6-trifluorobenzene

EXAMPLE 7

Preparation of 4-[4-trans-[4-(4-transpropylcyclohexyl)butyl]cyclohexyl]ethylbenzene (a compound of the formula (I) wherein R=n-$C_3H_7$, $X_1=X_3=H$ and $X_2=C_2H_5$)

The reaction step is divided into the following three steps:
1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.1 g) and THF (3 ml) were placed in a three-neck flask provided with a thermometer, a cooling tube and a dropping funnel, followed by dropwise adding and reacting a THF solution (10 ml) of 4-ethylbromobenzene (7.1 g) at room temperature over 30 minutes with stirring by a magnetic stirrer, aging with stirring for 2.5 hours while keeping the temperature at 50° C. in a hot bath, after completion of the dropwise addition, to prepare a Grignard reagent. The thus obtained compound is 4-ethylphenyl magnesium bromide. A THF solution (30 ml) of 4-[4-(trans-4-propylcyclohexyl)butyl]cyclohexanone (10 g) was dropwise added to the Grignard reagent over 30 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over magnesium sulfate, and distilling off the solvent under reduced pressure to obtain a reaction mixture (11.5 g). This is a mixture containing 4-[4-[4-(4-transpropylcyclohexyl)butyl]-1-hydroxycyclohexyl]ethylbenzene. The thus obtained reaction mixture was used in the subsequent dehydration reaction step, as it was.

2) In a three-neck flask provided with a drain tube, a cooling tube and a stirrer, the mixture containing 4-[4-[4-(4-transpropylcyclohexyl)butyl]-1-hydroxycyclohexyl]ethylbenzene (11.5 g) was dissolved in toluene (60 ml), followed by adding an acidic ion exchange resin for nonaqueous use as a catalyst (0.6 g), heating the mixture under reflux with stirring for one hour, filtering off the catalyst from the reaction solution, distilling off the solvent under reduced pressure and concentrating to obtain a reaction mixture (10.3 g). The thus obtained reaction mixture was purified according to silica gel-filled column chromatography, followed by recrystallizing from a mixed solvent of heptane-ethylacetate to obtain pale yellow crystals (6.6 g). The crystals are those of 4-[4-[4-(4-transpropylcyclohexyl)butyl]cyclohexen-1-yl]-ethylbenzene.

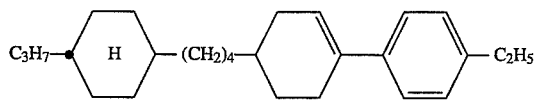

CN 66.6°–85.2° C., NI 99.9°–106.3° C.

3) In an egg-plant type flask, 4-[4-[4-(4-transpropylcyclohexyl)butyl]cyclohexen-1-yl]ethylbenzene (6.6 g) was dissolved in ethylacetate (50 ml), followed by adding a developing Raney nickel catalyst (4.0 g), subjecting the solution to catalytic hydrogenation under a hydrogen pressure of 5 to 10 kg/cm$^2$ at room temperature for 20 hours, filtering off the catalyst after completion of the reaction, distilling off the solvent under reduced pressure to obtain a reaction mixture (6.5 g). The trans substance was purified and recrystallized from a mixed solvent of heptaneethylacetate, to obtain white crystals (1.5 g). The crystals are those of 4-[4-[4-trans-(4-transpropylcyclohexyl)butyl]cyclohexyl]ethylbenzene.

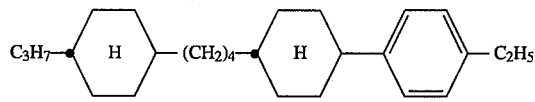

$S_A N$ 92.9°–97.3° C., NI 103.9°–106.0° C.

Using 4-[4-(trans-4-alkylcyclohexyl)butyl]cyclohexanones, each having different alkyl groups in place of 4-[4-(trans-4-propylcyclohexyl)butyl]cyclohexanone, the following 4-[4-trans-[4-(4-transalkylcyclohexyl)butyl]cyclohexyl]ethylbenzenes can be prepared according to the above preparation process:

4-[4-trans-[4-(4-transethylcyclohexyl)butyl]cyclohexyl]ethylbenzene

4-[4-trans-[4-(4-transbutylcyclohexyl)butyl]cyclohexyl]ethylbenzene

4-[4-trans-[4-(4-transpentylcyclohexyl)butyl]cyclohexyl]ethylbenzene

4-[4-trans-[4-(4-transhexylcyclohexyl)butyl]cyclohexyl]ethylbenzene

4-[4-trans-[4-(4-transheptylcyclohexyl)butyl]cyclohexyl]ethylbenzene

4-[4-trans-[4-(4-transoctylcyclohexyl)butyl]cyclohexyl]ethylbenzene

4-[4-trans-[4-(4-transnonylcyclohexyl)butyl]cyclohexyl]ethylbenzene

EXAMPLE 8

Preparation of 4-[4-trans-[4-(4-transpropylcyclohexyl)butyl]cyclohexyl]benzotrifluoride (a compound of the formula (I) wherein R=n-$C_3H_7$, $X_1=X_3=H$ and $X_2=CF_3$)

The reaction step is divided into the following three steps:
1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.1 g) and THF (3 ml) were placed in a three-neck flask provided with a thermometer, a cooling tube and a dropping funnel, followed by dropwise adding and reacting a THF solution (10 ml) of 4-bromobenzotrifluoride (7.1 g) at room temperature over 30 minutes with stirring by a magnetic stirrer, aging with stirring for 2.5 hours while keeping the temperature at 50° C. in a hot bath, after completion of the dropwise addition, to prepare a Grignard reagent. The thus obtained compound is 4-trifluoromethyl magnesium bromide. A THF solution (30 ml) of 4-[4-(trans-4-propylcyclohexyl)butyl]cyclohexanone (10 g) was dropwise added to the Grignard reagent over 30 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (400 ml) in this order, drying over magnesium sulfate, and distilling off the solvent under reduced pressure to obtain a reaction mixture (11.5 g). This is a mixture containing 4-[4-[4-(4-transpropylcyclohexyl)butyl]-1-hydroxycyclohexyl]benzotrifluoride. The reaction mixture was used in the subsequent dehydration reaction step, as ti was.

2) In a three-neck flask provided with a drain tube, a cooling tube and a stirrer, the mixture containing 4-[4-[4-(4-transpropylcyclohexyl)butyl]-1-hydroxycyclohexyl]benzotrifluoride (11.5 g) was dissolved in toluene (60 ml), followed by adding an acidic ion exchange resin for non-aqueous use as a catalyst (0.6 g), heating the mixture under reflux with stirring for one hour, filtering off the catalyst from the reaction solution, distilling off the solvent under reduced pressure and concentrating to obtain a reaction mixture (10.3 g). The thus obtained reaction mixture was purified according to silica gel-filled column chromatography, followed by recrystallizing from a mixed solvent of heptane-ethylacetate to obtain pale yellow crystals (6.6 g). The crystals are those of 4-[4-[4-(4-transpropylcyclohexyl)butyl]cyclohexen-1-yl]benzotrifluoride.

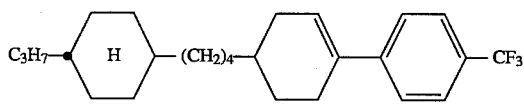

3) In an egg-plant type flask, 4-[4-[4-(4-transpropylcyclohexyl)butyl]cyclohexen-1-yl]benzotrifluoride (6.6 g) was dissolved in ethylacetate (50 ml), followed by adding a developing Raney nickel catalyst (5.0 g), subjecting the solution to catalytic hydrogenation under a hydrogen pressure of 5 to 10 kg/cm$^2$ at room temperature for 20 hours, filtering off the catalyst after completion of the reaction, distilling off the solvent under reduced pressure to obtain a reaction mixture (6.5 g). The trans substance of the reaction mixture was purified and recrystallized from a mixed solvent of heptane-ethylacetate, to obtain white crystals (1.5 g). The crystals are those of 4-[4-[4-trans-(4-transpropylcyclohexyl)butyl]cyclohexyl]benzotrifluoride.

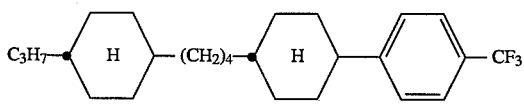

Using 4-[4-(trans-4-alkylcyclohexyl)butyl]cyclohexanones, each having different alkyl groups in place of 4-[4-(trans-4-propylcyclohexyl)butyl]cyclohexanone, the following 4-[4-trans-[4-(4-transalkylcyclohexyl)butyl]cyclohexyl]benzotrifluorides can be prepared according to the above preparation process:

4-[4-trans-[4-(4-transethylcyclohexyl)butyl]cyclohexyl]benzotrifluoride

4-[4-trans-[4-(4-transbutylcyclohexyl)butyl]cyclohexyl]benzotrifluoride

4-[4-trans-[4-(4-transpentylcyclohexyl)butyl]cyclohexyl]benzotrifluoride
C Sm 78.4°–78.9° C., Sm I 97.3°–98.2° C.

4-[4-trans-[4-(4-transhexylcyclohexyl)butyl]cyclohexyl]benzotrifluoride

4-[4-trans-[4-(4-transheptylcyclohexyl)butyl]cyclohexyl]benzotrifluoride

4-[4-trans-[4-(4-transoctylcyclohexyl)butyl]cyclohexyl]benzotrifluoride

4-[4-trans-[4-(4-transnonylcyclohexyl)butyl]cyclohexyl]benzotrifluoride

EXAMPLE 9

Preparation of 4-[4-trans-[4-(4-transpentylcyclohexyl)butyl]cyclohexyl]-2-fluorobenzotrifluoride (a compound of the formula (I) wherein R=n-$C_5H_{11}$, $X_1$=F, $X_3$=H and $X_2$=$CF_3$)

The reaction step is divided into the following three steps using 4-[4-trans-[4-(4-transpentylcyclohexyl)butyl]cyclohexyl]-2-fluorobenzene prepared in Example 3 as a raw material:

1) nitrogenation and reduction;

2) iodization and 3) trifluoromethylation.

The preparation steps will be described in more detail.

1) 4-[4-[4-trans-(4-transpentylcyclohexyl)butyl]cyclohexyl]-2-fluorobenzene (7.5 g) is dissolved in heptane (10 ml) in a three-neck flask provided with a thermometer, a cooling tube and a dropping funnel, followed by adding sulfuric acid (2 ml), and further adding nitric acid (2 ml) at room temperature with stirring by a magnetic stirrer, stirring at room temperature for 20 minutes after the addition, transferring the reaction solution into an ice-cooled water (100 ml) to complete the reaction, the reaction solution was transferred into a separating funnel to separate a heptane layer, followed by extracting the aqueous layer with heptane (50 ml), mixing the organic layers, washing with water (100 ml), a saturated aqueous solution of sodium carbonate (200 ml) and water (200 ml) in this order, drying over anhydrous magnesium sulfate, distilling off the solvent under reduced pressure, concentrating to obtain a reaction mixture (8.1 g). The reaction mixture was recrystallized from a mixed solvent of heptane-ethyl-acetate to obtain white crystals (3.5 g). The crystals are of 4-[4-[4-trans-(4-transpentylcyclohexyl)butyl]cyclohexyl]-2-fluoronitrobenzene. Then, in an egg-plant type flask, 4-[4-[4-trans-(4-transpentylcyclohexyl)butyl]cyclohexyl]-2-fluoronitrobenzene (3.5 g) was dissolved in ethylacetate (40 ml), followed by adding 5%-palladium-carbon catalyst (0.3 g), subjecting to a catalitic hydrogenation reaction at room temperature under reduced pressure of 5–10 kg/cm$^2$ for 4 hours, filtering off the catalyst from the reaction solution, distilling off the solvent under reduced pressure, and concentrating, to obtain a reaction mixture (3.6 g). This is 4-[4-[4-trans-(4-transpentylcyclohexyl)butyl]cyclohexyl]-2-fluoroaniline.

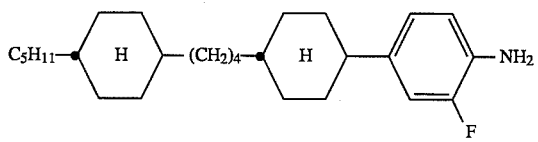

2) In a three-neck flask provided with a drain tube, a cooling tube and a stirrer, 4-[4-[4-trans-(4-transpentylcyclohexyl)butyl]cyclohexyl]-2-fluoroaniline (3.2 g) were fed, followed by dropwise adding an aqueous solution of sulfuric acid ($H_2SO_4$ 2 g/10 ml $H_2O$), stirring for 30 minutes after heating to 60° C., to convert the aniline derivative to the sulfate thereof. The generated sulfate was cooled down to 0° C. under ice-cooling, followed by dropwise adding over 5 minutes an aqueous solution (1.1 g/10 ml $H_2O$) of sodium nitrite under keeping the temperature at 0° C., and further stirring the reaction solution for one hour while keeping the temperature at 0° to 2° C., to age the generated diazonium salt, further dropwise adding an aqueous solution of potassium iodide (KI 2.0 g/2 ml H₂O) into the reaction solution at the same temperature after the aging, and stirring for one hour to complete the reaction. The reaction solution was transferred into a separation funnel after the temperature thereof was returned to room temperature, and being subjected to extraction with toluene (50 ml). The extracted layer was washed with an aqueous solution of saturated sodium carbonate (30 ml) and water (100 ml) in this order, followed by drying with anhydrous magnesium sulfate, distilling off the solvent under pressure, and concentrating, to obtain a reaction mixture (3.9 g). The obtained reaction mixture was recrystallized from a mixed solvent of heptane-ethylacetate to obtain white crystals (3.5 g). The crystals are those of 4-[4-[4-trans-(4-transpentylcyclohexyl)butyl]cyclohexyl]-2-fluoroiodobenzene.

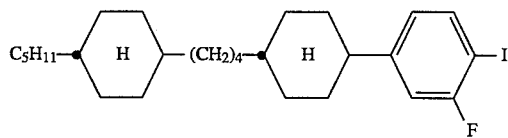

3) In an egg-plant type flask provided with a thermometer, a cooling tube and a nitrogen gas introducing tube, 4-[4-[4-trans-(4-transpenthylcyclohexyl)butyl]cyclohexyl]-2-fluoroiodobenzene (3.5 9) was dissolved in DMF (25 ml), followed by adding cuprous iodide (2.0 f) and fluorosulfonile (difluoro) methyl acetate (17.1 g) as a catalyst, and heating with stirring by a magnetic stirrer for 8 hours while keeping a temperature of 70°–80° C. under a nitrogen atmosphere. The reaction solution was cooled down to room temperature, followed by filtering off the catalyst, transferring it into a separating funnel, adding water (50 ml) and toluene (50 ml) to extract, washing an extracted layer with water (50 ml), a saturated aqueous solution of sodium carbonate (40 ml) and water (100 ml) in this order, drying over an anhydrous magnesium sulfate, distilling off the solvent under reduced pressure, and concentrating, to obtain a reaction mixture (3.1 g). The obtained reaction mixture was then purified according to silica gel-filled column chromatography using a mixed solvent of heptane-ethylacetate as a developing solvent, followed by repeating recrystallization from a mixed solvent of heptane-ethanol to obtain white crystals (1.0 g). The crystals are those of the objective 4-[4-[4-trans-(4-transpentylcyclohexyl)butyl]cyclohexyl]-2-fluorobenzotrifluoride.

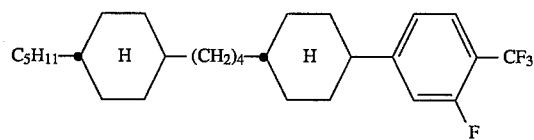

Sm I 78.6°–80.4° C.

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]-2-fluorobenzotrifluorides can be prepared according to the above preparation process:

4-[4-trans-[4-(4-transethylcyclohexyl)butyl]cyclohexyl]-2-fluorobenzotrifluoride 4-[4-trans-[4-(4-transpropylcyclohexyl)butyl]cyclohexyl]-2-fluorobenzotrifluoride 4-[4-trans-[4-(4-transbutylcyclohexyl)butyl]cyclohexyl]-2-fluorobenzotrifluoride 4-[4-trans-[4-(4-transhexylcyclohexyl)butyl]cyclohexyl]-2-fluorobenzotrifluoride 4-[4-trans-[4-(4-transheptylcyclohexyl)butyl]cyclohexyl]-2-fluorobenzotrifluoride 4-[4-trans-[4-(4-transoctylcyclohexyl)butyl]cyclohexyl]-2-fluorobenzotrifluoride 4-[4-trans-[4-(4-transnonylcyclohexyl)butyl]cyclohexyl]-2-fluorobenzotrifluoride

EXAMPLE 10

Preparation of 4-[4-trans-[4-(4-transpentylcyclohexyl)butyl]cyclohexyl]trifluoromethoxybenzene (a compound of the formula (I) wherein R=n-$C_5H_{11}$, $X_1$=$X_3$=H and $X_2$=$OCF_3$)

The reaction step is divided into the following three steps:

1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.1 g) and THF (3 ml) were placed in a three-neck flask provided with a thermometer, a cooling tube and a dropping funnel, followed by dropwise adding and reacting a THF solution (10 ml) of 4-trifluoromethoxybromobenzene (7.1 g) at room temperature over 30 minutes with stirring by a magnetic stirrer, aging with stirring for 2.5 hours while keeping the temperature at 50° C. in a hot bath, after completion of the dropwise addition, to prepare a Grignard reagent. The thus obtained compound is 4-trifluoromethoxyphenyl magnesium bromide. A THF solution (25 ml) of 4-[4-(trans-4-pentylcyclohexyl)butyl] cyclohexanone (10 g) was dropwise added to the Grignard reagent over 30 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over an anhydrous magnesium sulfate, and distilling off the solvent under reduced pressure to obtain a reaction mixture (11.5 g). This is a mixture containing 4-[4-[4-(4-transpentylcyclohexyl)butyl]-1-hydroxycyclohexyl]trifluoromethoxybenzene. The thus obtained reaction mixture was used in the subsequent dehydration reaction step, as it was.

2) In a three-neck flask provided with a drain tube, a cooling tube and a stirrer, 4-[4-[4-(4-transpentylcyclohexy-l)butyl]-1-hydroxycyclohexyl]trifluoromethoxybenzene (11.5 g) was dissolved in toluene (60 ml), followed by adding an acidic ion exchange resin for non-aqueous use as a catalyst (0.6 g), heating the mixture under reflux with stirring for one hour, filtering off the catalyst from the reaction solution, distilling off the solvent under reduced pressure and concentrating to obtain a reaction mixture (10.3 g). The thus obtained reaction mixture was purified according to silica gel-filled column chromatography, followed by recrystallizing from a mixed solvent of heptane-ethylacetate to obtain pale yellow crystals (8.3 g). The crystals are those of 4-[4-[4-(4transpentylcyclohexyl)butyl]cyclohexen-1-yl] trifluoromethoxybenzene.

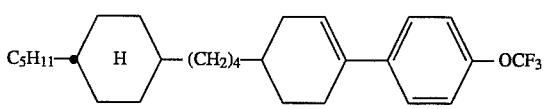

CN 43.2°–49.5° C., NI 94.1°–97.1° C.

3) In an egg-plant type flask, 4-[4-[4-(4-transpentylcyclohexyl)butyl]cyclohexene-1-yl]trifluoromethoxybenzene (8.3 g) was dissolved in ethylacetate (50 ml), followed by adding a developing Raney nickel catalyst (4.0 g), subjecting the solution to catalytic hydrogenation under a hydrogen pressure of 5 to 10 kg/cm² at room temperature for 20 hours, filtering off the catalyst after completion of the reaction, distilling off the solvent under reduced pressure to obtain a reaction mixture (8.5 g). The trans substance in the reaction mixture was purified by recrystallization from a mixed solvent of heptane-ethylacetate, to obtain white crystals (3.5 g). The crystals are those of 4-[4-[4-trans-(4-transpentylcyclohexyl)butyl]cyclohexyl]trifluoromethoxybenzene.

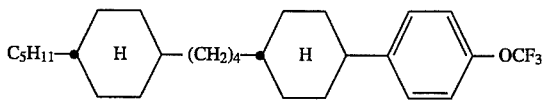

CN 65.0°–67.3° C., NI 102.8°–104.0° C.

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]trifluoromethoxybenzenes can be prepared according to the above preparation process:

4-[4-trans-[4-(4-transethylcyclohexyl)butyl]cyclohexyl] trifluoromethoxybenzene

4-[4-trans-[4-(4-transpropylcyclohexyl)butyl]cyclohexyl] trifluoromethoxybenzene 4-[4-trans-[4-(4-transbutylcyclohexyl)butyl]cyclohexyl] trifluoromethoxybenzene 4-[4-trans-[4-(4-transhexylcyclohexyl)butyl]cyclohexyl] trifluoromethoxybenzene 4-[4-trans-[4-(4-transheptylcyclohexyl)butyl]cyclohexyl] trifluoromethoxybenzene 4-[4-trans-[4-(4-transoctylcyclohexyl)butyl]cyclohexyl] trifluoromethoxybenzene 4-[4-trans-[4-(4-transnonylcyclohexyl)butyl]cyclohexyl] trifluoromethoxybenzene

EXAMPLE 11

Preparation of 4-[4-trans-[4-(4-transpentylcyclohexyl)butyl]cyclohexyl]-2-fluorotrifluoromethoxybenzene (a compound of the formula (I) wherein R=n-$C_5H_{11}$, $X_1$=F, $X_3$=H and $X_2$=$OCF_3$)

The reaction step is divided into the following three steps:
1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.1 g) and THF (3 ml) were placed in a three-neck flask provided with a thermometer, a cooling tube and a dropping funnel, followed by dropwise adding and reacting a THF solution (15 ml) of 3-fluoro-4-trifluoromethoxybromobenzene (10.9 g) at room temperature over 20 minutes with stirring by a magnetic stirrer, aging with stirring for 2.5 hours while keeping the temperature at 50° C. in a hot bath, after completion of the dropwise addition, to prepare a Grignard reagent. The thus obtained compound is 3-fluoro-4-trifluoromethoxyphenylmagnesium bromide. A THF solution (30 ml) of 4-[4-(trans-4-pentylcyclohexyl)butyl]cyclohexanone (10 g) was dropwise added to the Grignard reagent over 30 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over magnesium sulfate, and distilling off the solvent under reduced pressure to obtain a reaction mixture (15.5 g). This is a mixture containing 4-[4-[4-(4-transpentylcyclohexyl)butyl]-1-hydroxycyclohexyl]-2-fluorotrifluoromethoxybenzene. The thus obtained reaction mixture was used in the subsequent dehydration reaction step, as it was. 2) In a three-neck flask provided with a drain tube, a cooling tube and a stirrer, the mixture containing 4-[4-[4-(4-transpentylcyclohexyl)butyl]-1-hydroxycyclohexyl] -2-fluorotrifluoromethoxybenzene (15.5 g) was dissolved in toluene (80 ml), followed by adding an acidic ion exchange resin for non-aqueous use as a catalyst (0.8 g), heating the mixture under reflux with stirring for one hour, filtering off the catalyst from the reaction solution, distilling off the solvent under reduced pressure and concentrating to obtain a reaction mixture (14.5 g). The thus obtained reaction mixture was purified according to silica gel-filled column chromatography, followed by recrystallizing from a mixed solvent of heptane-ethylacetate to obtain pale yellow crystals (9.8 g). The crystals are those of 4-[4-[4-(4-transpentylcyclohexyl)butyl]cyclohexen-1-yl]-2-fluorotrifluoromethoxybenzene.

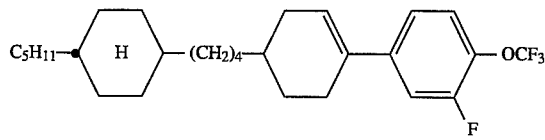

3) In an egg-plant type flask, 4-[4-[4-(4-transpentylcyclohexyl)butyl]cyclohexen-1-yl]-2-fluorotrifluoromethoxybenzene (9.8 g) was dissolved in ethylacetate (80 ml), followed by adding a developing Raney nickel catalyst (6.0 g), subjecting the solution to catalytic hydrogenation under a hydrogen pressure of 5 to 10 kg/cm² at room temperature for 20 hours, filtering off the catalyst after completion of the reaction, distilling off the solvent under reduced pressure to obtain a reaction mixture (9.7 g). The trans substance of the reaction mixture was purified by recrystallization from a mixed solvent of heptane-ethylacetate, to obtain white crystals (2.9 g). The crystals are those of 4-[4-[4-trans-(4-transpentylcyclohexyl)butyl]cyclohexyl]-2-fluorotrifluoromethoxybenzene.

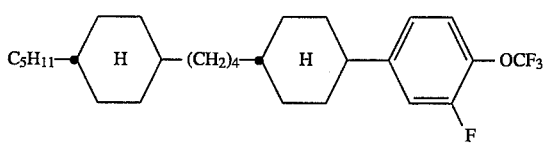

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]-2-fluorotrifluoromethoxybenzene can be prepared according to the above preparation process:

- 4-[4-trans-[4-(4-transethylcyclohexyl)butyl]cyclohexyl]-2-fluorotrifluoromethoxybenzene
- 4-[4-trans-[4-(4-transpropylcyclohexyl)butyl]cyclohexyl]-2-fluorotrifluoromethoxybenzene
- 4-[4-trans-[4-(4-transbutylcyclohexyl)butyl]cyclohexyl]-2-fluorotrifluoromethoxybenzene
- 4-[4-trans-[4-(4-transhexylcyclohexyl)butyl]cyclohexyl]-2-fluorotrifluoromethoxybenzene
- 4-[4-trans-[4-(4-transheptylcyclohexyl)butyl]cyclohexyl]-2-fluorotrifluoromethoxybenzene
- 4-[4-trans-[4-(4-transoctylcyclohexyl)butyl]cyclohexyl]-2-fluorotrifluoromethoxybenzene
- 4-[4-trans-[4-(4-transnonylcyclohexyl)butyl]cyclohexyl]-2-fluorotrifluoromethoxybenzene

EXAMPLE 12

Preparation of 4-[4-trans-[4-(4-transpentylcyclohexyl)butyl]cyclohexyl]-2,6-difluorotrifluoromethoxybenzene (a compound of the formula (I) wherein R=n-$C_5H_{11}$ and $X_1=X_3=F$ and $X_2=OCF_3$)

The reaction step is divided into the following three steps:
1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.1 g) and THF (3 ml) were placed in a three-neck flask provided with a thermometer, a cooling tube and a dropping funnel, followed by dropwise adding and reacting a THF solution (25 ml) of 3,5-difluoro-4-trifluoromethoxybromobenzene (11.8 g) at room temperature over 30 minutes with stirring by a magnetic stirrer, aging with stirring for 2.5 hours while keeping the temperature at 50° C. in a hot bath, after completion of the dropwise addition, to prepare a Grignard reagent. The thus obtained compound is 3,5-difluoro-4-trifluoromethoxyphenyl magnesium bromide. A THF solution (30 ml) of 4-[4-(trans-4-pentylcyclohexyl)butyl]cyclohexanone (10 g) was dropwise added to the Grignard reagent over 30 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by washing with water (100 ml), a saturated aqueous solution of sodium carbonate (50 ml) and water (200 ml) in this order, drying over magnesium sulfate, and distilling off the solvent under reduced pressure to obtain a reaction mixture (16.3 g). This is a mixture containing 4-[4-[4-(4-transpentylcyclohexyl)butyl]-1-hydroxycyclohexyl]-2,6-difluorotrifluoromethoxybenzene. The thus obtained reaction mixture was used in the subsequent dehydration reaction step, as ti was.

2) In a three-neck flask provided with a drain tube, a cooling tube and a stirrer, the mixture containing 4-[4-[4-(4-transpentylcyclohexyl)butyl]-1-hydroxycyclohexyl]-2,6-difluorotrifluoromethoxybenzene (16.3 g) was dissolved in toluene (90 ml), followed by adding an acidic ion exchange resin for non-aqueous use as a catalyst (0.8 g), heating the mixture under reflux with stirring for one hour, filtering off the catalyst from the reaction solution, distilling off the solvent under reduced pressure and concentrating to obtain a reaction mixture (15.5 g). The thus obtained reaction mixture was purified according to silica gel-filled column chromatography, followed by recrystallizing from a mixed solvent of heptane-ethylacetate to obtain white crystals (13.1 g). The crystals are those of 4-[4-[4-(4-transpentylcyclohexyl)butyl]cyclohexen-1-yl]-2,6-difluorotrifluoromethoxybenzene.

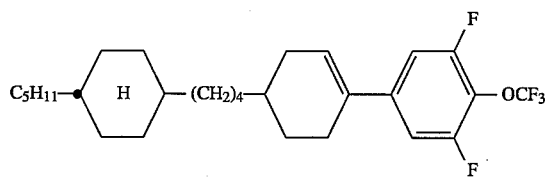

3) In an egg-plant type flask, 4-[4-[4-(4-transpentylcyclohexyl)butyl]cyclohexen-1-yl]-2,6-difluorotrifluoromethoxybenzene (13.1 g) was dissolved in ethylacetate (80 ml), followed by adding a developing Raney nickel catalyst (8.0 g), subjecting the solution to catalytic hydrogenation under a hydrogen pressure of 5 to 10 kg/cm$^2$ at room temperature for 20 hours, filtering off the catalyst after completion of the reaction, distilling off the solvent under reduced pressure to obtain a reaction mixture (13.0 g). The trans substance of the reaction mixture was purified by recrystallizing from a mixed solvent of heptane-ethylacetate, to obtain white crystals (3.3 g). The crystals are those of 4-[4-[4-trans-(4-transpentylcyclohexyl)butyl]cyclohexyl]-2,6-difluorotrifluoromethoxybenzene.

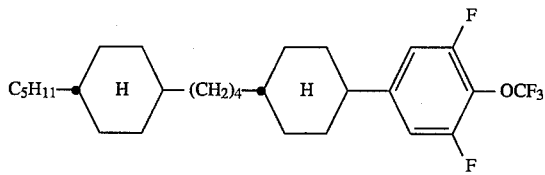

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]-2,6-difluorotrifluoromethoxybenzenes can be prepared according to the above preparation process:

- 4-[4-trans-[4-(4-transethylcyclohexyl)butyl]cyclohexyl]-2,6-difluorotrifluoromethoxybenzene
- 4-[4-trans-[4-(4-transpropylcyclohexyl)butyl]cyclohexyl]-2,6-difluorotrifluoromethoxybenzene
- 4-[4-trans-[4-(4-transbutylcyclohexyl)butyl]cyclohexyl]-2,6-difluorotrifluoromethoxybenzene
- 4-[4-trans-[4-(4-transhexylcyclohexyl)butyl]cyclohexyl]-2,6-difluorotrifluoromethoxybenzene
- 4-[4-trans-[4-(4-transheptylcyclohexyl)butyl]cyclohexyl]

-2,6-difluorotrifluoromethoxybenzene

4-[4-trans-[4-(4-transoctylcyclohexyl)butyl]cyclohexyl]-2,6-difluorotrifluoromethoxybenzene 4-[4-trans-[4-(4-transnonylcyclohexyl)butyl]cyclohexyl]-2,6-difluorotrifluoromethoxybenzene

EXAMPLE 13

Preparation of 4-[4-trans-[4-(4-transpentylcyclohexyl)butyl]cyclohexyl]-2,6-difluorobenzotrifluoride (a compound of the formula (I) wherein R=n-$C_5H_{11}$, $X_1=X_3=F$ and $X_2=CF_3$)

The reaction step is divided into the following three steps:
1) Grignard reaction;
2) dehydration reaction of alcohol; and
3) catalytic hydrogenation of cyclohexene derivative.

The preparation steps will be described in more detail.

1) Preparation of Grignard reagent was carried out in a conventional manner. Mg (1.9 g) and THF (3 ml) were placed in a three-neck flask provided with a thermometer, a cooling tube and a dropping funnel, followed by dropwise adding and reacting a THF solution (20 ml) of 4-bromo-2,6-difluorobenzotrifluoride (19.1 g) at room temperature over 40 minutes with stirring by a magnetic stirrer, aging with stirring for 2.5 hours while keeping the temperature at 50° C. in a hot bath, after completion of the dropwise addition, to prepare a Grignard reagent. The thus obtained compound is 3,5-difluoro-4-trifluoromethylphenyl magnesium bromide. A THF solution (30 ml) of 4-[4-(trans-4-pentylcyclohexyl)butyl]cyclohexanone (15 g) was dropwise added to the Grignard reagent over 40 minutes so as to keep the temperature inside the system at 40° to 60° C., after the aging, followed by aging at the same temperature for 5 hours, cooling with ice after the aging, adding 6N HCl aqueous solution (40 ml) to complete the reaction. The reaction solution was transferred into a separating funnel, followed by extracting with ethylacetate (100 ml), washing with water (100 ml), a saturated aqueous solution of sodium carbonate (50 ml) and water (200 ml) in this order, drying over an anhydrous magnesium sulfate, and distilling off the solvent under reduced pressure to obtain a reaction mixture (22.9 g). This is a mixture containing 4-[4-[4-(4-transpentylcyclohexyl)butyl]-1-hydroxycyclohexyl]-2,6-difluorobenzotrifluoride. The thus obtained reaction mixture was used in the subsequent dehydration reaction step, as ti was.

2) In a three-neck flask provided with a drain tube, a cooling tube and a stirrer, the mixture containing 4-[4-[4-(4-transpentylcyclohexyl)butyl]-1-hydroxycyclohexyl]-2,6-difluorobenzotrifluoride (22.9 g) was dissolved in toluene (130 ml), followed by adding an acidic ion exchange resin for non-aqueous use as a catalyst (1.1 g), heating the mixture under reflux with stirring for one hour, filtering off the catalyst from the reaction solution, distilling off the solvent under reduced pressure and concentrating to obtain a reaction mixture (19.8 g). The thus obtained reaction mixture was purified according to silica gel-filled column chromatography, followed by recrystallizing from a mixed solvent of heptane-ethylacetate to obtain pale yellow crystals (2.9 g). The crystals are those of 4-[4-[4-(4-transpentylcyclohexyl)butyl]cyclohexen-1-yl]-2,6-difluorobenzotrifluoride.

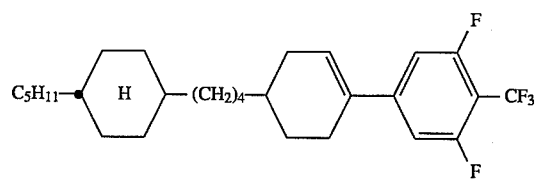

CN 58.0°–61.9° C., NI 63.3°–64.9° C.

3) In an egg-plant type flask, 4-[4-[4-(4-transpentylcyclohexyl)butyl]cyclohexen-1-yl]-2,6-difluorobenzotrifluoride (2.9 g) was dissolved in a mixed solution of toluene:solmix=1:1 (30 ml), followed by adding palldiumcarbon (0.2 g), subjecting the solution to catalytic hydrogenation under a hydrogen pressure of 5 to 10 kg/cm$^2$ at room temperature for 20 hours, filtering off the catalyst after completion of the reaction, distilling off the solvent under reduced pressure to obtain a reaction mixture (3.1 g). The trans substance of the reaction mixture was purified by recrystallizing from a mixed solvent of heptane-ethylacetate, to obtain white crystals (1.5 g). The crystals are those of 4-[4-[4-trans-(4-transpentylcyclohexyl)butyl]cyclohexyl]-2,6-difluorobenzotrifluoride.

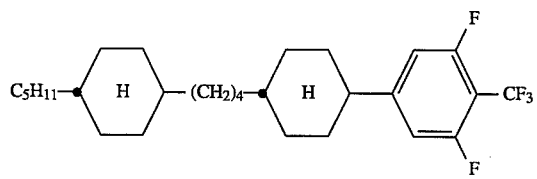

SmI 68.5°–71.0° C.

Using 4-[4-(trans-4-alkylcyclohexyl)butyl]cyclohexanones, each having different alkyl groups in place of 4-[4-(trans-4-pentylcyclohexyl)butyl]cyclohexanone, the following 4-[4-trans-[4-(4-transalkylcyclohexyl)butyl]cyclohexyl]-2,6-difluorobenzotrifluoride can be prepared according to the above preparation process:

4-[4-trans-[4-(4-transethylcyclohexyl)butyl]cyclohexyl]-2,6-difluorobenzotrifluoride 4-[4-trans-[4-(4-transbutylcyclohexyl)butyl]cyclohexyl]-2,6-difluorobenzotrifluoride 4-[4-trans-[4-(4-transhexylcyclohexyl)butyl]cyclohexyl]-2,6-difluorobenzotrifluoride 4-[4-trans-[4-(4-transheptylcyclohexyl)butyl]cyclohexyl]-2,6-difluorobenzotrifluoride 4-[4-trans-[4-(4-transoctylcyclohexyl)butyl]cyclohexyl]-2,6-difluorobenzotrifluoride 4-[4-trans-[4-(4-transnonylcyclohexyl)butyl]cyclohexyl]-2,6-difluorobenzotrifluoride

EXAMPLE 14 (USE EXAMPLE 1)

A nematic liquid crystal of the liquid crystal composition consisting of 4-(4-propylcyclohexyl)benzonitrile 30% by weight, 4-(4-pentylcyclohexyl)benzonitrile 40% by weight, and 4-(4-heptylcyclohexyl)benzonitrile 30% by weight, had a clearing point (Cp) of 52.3° C. This liquid crystal composition was sealed in a TN cell (twisted nematic cell) having a cell depth of 9 m and the physical properties thereof were measured. As a result, the threshold voltage ($V_{th}$) was 1.6 V, the dielectric anisotropy value (Δε) was +10.7, the optical anisotropy (Δn) was 0.119, and the viscosity was 21.7 cp. This liquid crystal composition is referred to as composition A.

A compound of the present invention, 4-[4-trans-[4-(4-transpentylcyclohexyl)butyl]cyclohexyl]benzonitrile (15%) was mixed with the composition A (85%) as a mother liquid crystal composition. The physical properties of the resulting composition were measured. The results were as follows:

Cp=68.6° C., Δε=10.5, Δn=0.123, η$_{20}$=26.1 cp, and V$_{th}$=1.72 V.

Further, when this composition was allowed to stand in a freezer at −20° C. for 20 days, no deposition of crystals was observed.

EXAMPLE 15 (USE EXAMPLE 2)

A compound of the present invention, 4-[4-trans-[4-(4-transpropylcyclohexyl)butyl]cyclohexyl]fluorobenzene (15%) was mixed with the composition A shown in Use example 1 as a mother liquid crystal composition, and the physical properties of the resulting composition were measured. The results are as follows:

Cp=58.8° C., Δε=9.7, Δn=0.113, η$_{20}$=22.2 cp, and V$_{th}$=1.58 V.

Further, when this composition was allowed to stand in a freezer at −20° C. for 20 days, no deposition of crystals was observed.

Further, the liquid crystal composition consisting of

4-[trans-4-(trans-4-ethylcyclohexyl)cyclohexyl]-1,2-difluorobenzene 33% by weight, 4-[trans-4-(trans-4-propylcyclohexyl)cyclohexyl]-1,2-difluorobenzene 33% by weight, and 4-[trans-4-(trans-4-pentylcyclohexyl)cyclohexyl]-1,2-difluorobenzene 33% by weight, had a clearing point (Cp) of 112.3° C. This liquid crystal composition was sealed in a TN cell having a cell depth of 8.7 μm and physical properties thereof were measured. The results were as follows:

V$_{th}$=2.3 V, Δε=5.0, Δn=0.079, η$_{20}$=25.8.

This liquid crystal composition was referred to as composition B.

Physical properties were similarly measured as to a composition having used composition B as a mother liquid crystal composition. The results were as follows:

Cp=109.8, Δε=4.6, Δn=0.078, η$_{20}$=22.6 cp, and V$_{th}$=2.46 V.

When this composition was allowed to stand in a freezer at −20° C. for 20 days, no deposition of crystals was observed.

EXAMPLE 16 (USE EXAMPLE 3)

A compound of the present invention, 4-[4-trans-[4-(4-transpentylcyclohexyl)butyl]cyclohexyl]-1,2,6-trifluorobenzene (15%) was mixed with the composition A shown in Use example 1 as a mother liquid crystal composition and physical properties of the resulting composition were measured. The results were as follows:

Cp=54.0° C., Δε=10.2, Δn=0.111, η$_{20}$=23.3 cp, and V$_{th}$=1.47 V.

Further, when this composition was allowed to stand in a freezer at −20° C. for 20 days, no deposition of crystals was observed.

EXAMPLE 17 (USE EXAMPLE 4)

A compound of the present invention, 4-[4-trans-[4-(4-transpentylcyclohexyl)butyl]cyclohexyl]trifluoromethoxybenzene (15%) was mixed with the composition A shown in Use example 1 as a mother liquid crystal composition and physical properties of the resulting composition were measured. The results were as follows:

Cp=57.8° C., Δε=9.8, Δn0.114, η$_{20}$=21.4 cp, and V$_{th}$=1.57 V.

Further, when this compound was allowed to stand in a freezer at −20° C. for 20 days, no deposition of crystals was observed.

Further, physical properties were similarly measured as to a composition having used composition B as a mother liquid crystal composition. The results were as follows:

Cp=110.2° C., Δε=4.8, Δn=0.079, η$_{20}$=23.2 cp, and V$_{th}$=2.42 V.

When this composition was allowed to stand in a freezer at −20° C. for 20 days, no deposition of crystals was not observed.

What we claim is:

1. A phenyl-4-cyclohexylbutylcyclohexane derivative expressed by the formula

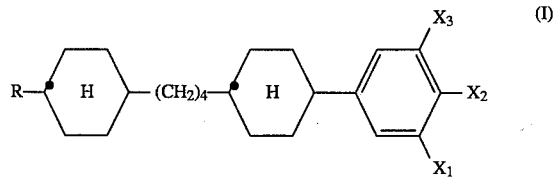

wherein R represents a hydrogen atom or a linear or branched alkyl group of 1 to 15 carbon atoms, and $X_1$, $X_2$ and $X_3$ are each independent and $X_1$ and $X_3$ each represent a hydrogen atom or a halogen atom and $X_2$ represents (1) a hydrogen atom, (2) a linear or branched alkyl group of 1 to 15 carbon atoms, wherein one —CH$_2$CH$_2$— bond may be replaced by a —CH=CH— bond and one non-adjacent —CH$_2$— bond may be replaced by an oxygen atom, (3) a halogen atom, (4) a cyano group, (5) a trifluoromethyl group or (6) a trifluoromethoxy group.

2. A 4-[4-trans-[4-(4-transalkylcyclohexyl)butyl]cyclohexyl]benzonitrile, a compound of the formula (I) according to claim 1, wherein R represents a hydrogen atom or a linear or branched alkyl group of 1 to 15 carbon atoms, $X_1$ represents a hydrogen atom, $X_2$ represents a cyano group and $X_3$ represents a hydrogen atom.

3. A 4-[4-trans-[4-(4-transalkylcyclohexyl)butyl]cyclohexyl]-2-fluorobenzonitrile, a compound of the formula (I) according to claim 1, wherein R represents a hydrogen atom or a linear or branched alkyl group of 1 to 15 carbon atoms, $X_1$ represents a fluorine atom, $X_2$ represents a cyano group and $X_3$ represents a hydrogen atom.

4. A 4-[4-trans-[4-(4-transalkylcyclohexyl)butyl]cyclohexyl]fluorobenzene, a compound of the formula (I) according to claim 1, wherein R represents a hydrogen atom or a linear or branched alkyl group of 1 to 15 carbon atoms, $X_1$ and $X_3$ each represents a hydrogen atom and $X_2$ represents a fluorine atom.

5. A 4-[4-trans-[4-(4-transalkylcyclohexyl)butyl]cyclohexyl]-1,2-difluorobenzene, a compound of the formula (I) according to claim 1, wherein R represents a hydrogen atom or a linear or branched alkyl group of 1 to 15 carbon atoms, $X_1$ represents a fluorine atom, $X_3$ represents a harogen atom and $X_2$ represents a fluorine atom.

6. A 4-[4-trans-[4-(4-transalkylcyclohexyl)butyl]cyclohexyl]-1,2,6-trifluorobenzene, a compound of the formula (I) according to claim 1, wherein R represents a hydrogen atom or a linear or branched alkyl group of 1 to 15 carbon atoms and $X_1$, $X_2$ and $X_3$ each represent a fluorine atom.

7. A 4-[4-trans-[4-(4-transalkylcyclohexyl)butyl]cyclohexyl]alkylbenzene, a compound of the formula (I) according to claim 1, wherein R represents a hydrogen atom or a linear or branched alkyl group of 1 to 15 carbon atoms, $X_1$ represents a hydrogen atom or a fluorine atom, $X_2$ represents a hydrogen atom or a linear or branched alkyl group of 1 to 15 carbon atoms (wherein one —$CH_2CH_2$— bond can be a —CH=CH— bond and one non-adjacent —$CH_2$— bond can be replaced by an oxygen atom), and $X_3$ represents a hydrogen atom.

8. A 4-[4-trans-[4-(4-transalkylcyclohexyl)butyl]cyclohexyl]benzotrifluoride, a compound of the formula (I) according to claim 1, wherein R represents a hydrogen atom or a linear or branched alkyl group of 1 to 15 carbon atoms, $X_1$ represents a hydrogen atom or a fluorine atom, $X_2$ represents a trifluoromethyl group and $X_3$ represents a hydrogen atom.

9. A 4-[4-trans-[4-(4-transalkylcyclohexyl)butyl]cyclohexyl]trifluoromethoxybenzene, a compound of the formula (I) according to claim 1, wherein R represents a hydrogen atom or a linear or branched alkyl group of 1 to 15 carbon atoms, $X_1$ and $X_3$ each represent a hydrogen atom and $X_2$ represents a trifluoromethoxy group.

10. A 4-[4-trans-[4-(4-transalkylcyclohexyl)butyl]cyclohexyl]-2-fluorotrifluoromethoxybenzene, a compound of the formula (I) according to claim 1, wherein R represents a hydrogen atom or a linear or branched alkyl group of 1 to 15 carbon atoms, $X_1$ represents a fluorine atom, $X_3$ represents a hydrogen atom and $X_2$ represents a trifluoromethoxy group.

11. A 4-[4-trans-[4-(4-transalkylcyclohexyl)butyl]cyclohexyl]-2,6-difluorotrifluoromethoxybenzene, a compound of the formula (I) according to claim 1, wherein R represents a hydrogen atom or a linear or branched alkyl group of 1 to 15 carbon atoms, $X_1$ and $X_3$ each represent a fluorine atom and $X_2$ represents a trifluoromethoxy group.

12. A liquid crystal composition comprising at least two liquid crystalline components at least one of which is a compound as set forth in claim 1.

* * * * *